(12) United States Patent
Diefenbacher et al.

(10) Patent No.: US 7,723,549 B2
(45) Date of Patent: May 25, 2010

(54) PROCESS FOR PREPARING AT LEAST ONE TARGET PRODUCT BY PARTIAL OXIDATION AND/OR AMMOXIDATION OF PROPYLENE

(75) Inventors: Armin Diefenbacher, Germersheim (DE); Claus Hechler, Ludwigshafen (DE); Christoph Adami, Weinheim (DE); Martin Dieterle, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1032 days.

(21) Appl. No.: 11/411,882

(22) Filed: Apr. 27, 2006

(65) Prior Publication Data

US 2006/0258529 A1 Nov. 16, 2006

Related U.S. Application Data

(60) Provisional application No. 60/679,971, filed on May 12, 2005.

(30) Foreign Application Priority Data

May 12, 2005 (DE) .................. 10 2005 022 798

(51) Int. Cl.
C07C 45/28 (2006.01)
C07C 51/25 (2006.01)
C07C 253/24 (2006.01)

(52) U.S. Cl. .................. 568/475; 568/469.9; 568/476; 568/479; 562/512.2; 562/542; 558/323; 549/524

(58) Field of Classification Search ............. 568/469.9, 568/475, 476, 479; 562/512.2; 549/524
See application file for complete search history.

(56) References Cited

U.S. PATENT DOCUMENTS

| 2004/0063988 A1 | 4/2004 | Hechler et al. |
| 2004/0063989 A1 | 4/2004 | Hechler et al. |
| 2004/0116741 A1 | 6/2004 | Nordhoff et al. |
| 2004/0199001 A1 | 10/2004 | Schindler et al. |
| 2005/0222459 A1 | 10/2005 | Nordhoff et al. |

FOREIGN PATENT DOCUMENTS

| DE | 102 45 585 A1 | 4/2004 |
| DE | 102 46 119 A1 | 4/2004 |
| DE | 103 16 039 A1 | 10/2004 |
| WO | WO 97/36849 | * 10/1997 |
| WO | WO 02/055469 A1 | 7/2002 |
| WO | WO 03/078378 A1 | 9/2003 |

* cited by examiner

*Primary Examiner*—Bernard Dentz
(74) *Attorney, Agent, or Firm*—Oblon, Spivak, McClelland, Maier & Neustadt, L.L.P.

(57) ABSTRACT

A process for preparing at least one target product by partial oxidation and/or ammoxidation of propylene, in which the propylene source used is a propane dehydrogenation, the propane used therein being obtained by a rectificative prepurification of crude propane.

70 Claims, No Drawings

PROCESS FOR PREPARING AT LEAST ONE TARGET PRODUCT BY PARTIAL OXIDATION AND/OR AMMOXIDATION OF PROPYLENE

The present invention relates to a process for preparing at least one target product P by partial oxidation and/or ammoxidation of propylene, by a) subjecting prepurified propane, in a first reaction step in the presence of and/or with exclusion of molecular oxygen, to at least one dehydrogenation from the group comprising homogeneous dehydrogenation, heterogeneously catalyzed dehydrogenation, homogeneous oxydehydrogenation and heterogeneously catalyzed oxydehydrogenation to obtain a gas mixture 1 comprising unconverted propane and formed propylene, and b) if appropriate, removing a portion or the entirety of the constituents other than propane and propylene present in the entirety or in a portion of gas mixture 1 therefrom and/or converting them to other compounds to obtain a gas mixture 1' comprising propane and propylene, and, in at least one further reaction step c) subjecting gas mixture 1 or gas mixture 1' or a mixture of formed gas mixture 1' and remaining gas mixture 1, as a constituent of a gas mixture 2, to a heterogeneously catalyzed gas phase partial oxidation and/or partial gas phase ammoxidation of propylene present in gas mixture 1 and/or gas mixture 1' to obtain a gas mixture 3 comprising at least one target product P, d) removing target product from gas mixture 3 in at least one removal step and, of the remaining residual gas, recycling at least propane into the first reaction step.

As a partial oxidation product of propylene, acrylic acid is a significant monomer which finds use, as such or in the form of its alkyl esters, for obtaining, for example, polymers useful as adhesives or that superabsorb water (cf., for example, WO 02/055469 and WO 03/078378). Quite generally, the partial oxidation and/or ammoxidation products of propylene are important intermediates for the preparation of polymers and the other propylene partial oxidation or ammoxidation products (e.g. acrolein, acrylonitrile, propylene oxide).

The preparation of acrylic acid and other propylene partial oxidation products by the process described at the outset is known (cf., for example, DE-A 102 45 585 and DE-A 102 46 119).

It is likewise known from the aforementioned documents that the gas mixture 2 in such a process should be substantially free of $C_4$ hydrocarbons ($C_4$ HC for short) (in this document, this refers to all compounds which are composed of 4 carbon atoms and hydrogen; these include n-butane, isobutane, trans-butene-2, cis-butene-2, butene-1, isobutene, butadiene-1,3, butadiene-1,2, 1-butyne and 2-butyne; correspondingly, $C_2$ hydrocarbons are compounds composed of 2 carbon atoms and hydrogen ($C_2$ HC); these include in particular ethane and ethylene; acetylene is of rather minor importance since, unlike ethane and ethylene, it typically occurs in rather negligible amounts as a propane companion), since these compounds generally poison the catalysts required in the partial oxidation. As a possible measure of remedy, both documents recommend, if appropriate, undertaking a rectificative preremoval of $C_4$ hydrocarbons present in crude propane.

It is also known from the abovementioned documents that $C_2$ hydrocarbons are not such catalyst poisons, which is why DE-A 102 45 585 and DE-A 102 46 119 do not have any analogous specification for $C_2$ hydrocarbons in gas mixture 2. Rather, it is assumed in both documents that $C_2$ hydrocarbons (especially ethane but also ethylene) behave as inert diluent gases in the partial oxidation. However, inert behavior in the context of a cycle gas method described at the outset is disadvantageous in that the $C_3$ HC circuit necessarily requires an outlet (i.e. a $C_2$ HC removal from $C_3$ HC) for such inert constituents, since they would otherwise accumulate in an unrestricted manner in the cycle method. When the crude propane comprises, in addition to $C_4$ HC, simultaneously. $C_2$ HC as impurities (which is generally the case), at least one $C_2$ HC outlet (especially in the case of ethane and ethylene as $C_2$ HC impurities of crude propane) would therefore normally be combined with a rectificative $C_4$ HC preremoval of $C_4$ hydrocarbons present in crude propane, since the crude propane stream, in comparison to all gas streams within the cycle system, both in terms of its chemical composition and in terms of its volume, is a gas stream which is comparatively simple and uncomplicated to handle.

Conversely, such a $C_2$ preremoval would be very substantially dispensed with if the cycle to be passed through by propane in the relevant process were to have, by its nature, an outlet for $C_2$ HC (such an outlet exists, by the nature of the process, prima facie exclusively for the at least one target product P). This is not least because rectificative separations of mixtures comprising $C_2$ to $C_4$ HC always have to be undertaken under elevated pressure. Otherwise, particularly low temperatures are required to obtain the reflux liquid required within the rectification column. However, the more theoretical plates are required in a rectification column, the greater the complexity of construction to be undertaken for a pressure column (for example merely for reasons of safe statics).

According to the invention, it has now been found that, surprisingly, especially the $C_2$ hydrocarbons ethane and ethylene, as routine companions of propane in crude propane, under the conditions of a heterogeneously catalyzed partial oxidation and/or ammoxidation of propylene to, for example, acrolein, acrylic acid, propylene oxide and/or acrylonitrile, are normally inert only to such an extent that a natural outlet of $C_2$ HC present in the gas mixture 2 is ensured in the context of the cycle gas method. Both ethane and ethylene are oxidized under the customary conditions of a propylene partial oxidation and/or ammoxidation in a sufficient manner to acetonitrile, acetaldehyde and/or acetic acid that a $C_2$ HC outlet in the form of acetonitrile, acetic acid and/or acetaldehyde (all of which are more similar to the target product than the $C_2$ HC precursors) generally accompanies the target product removal in a sufficient manner.

Accordingly, in accordance with the invention, a process is provided for preparing at least one target product P by partial oxidation and/or ammoxidation of propylene, by a) subjecting prepurified propane, in a first reaction step in the presence of and/or with exclusion of molecular oxygen, to at least one dehydrogenation from the group comprising homogeneous dehydrogenation, heterogeneously catalyzed dehydrogenation, homogeneous oxydehydrogenation and heterogeneously catalyzed oxydehydrogenation to obtain a gas mixture 1 comprising unconverted propane and formed propylene, and b) if appropriate, removing a portion or the entirety of the constituents other than propane and propylene present in the entirety or in a portion of gas mixture 1 therefrom and/or converting them to other compounds to obtain a gas mixture 1' comprising propane and propylene, and, in at least one further reaction step c) subjecting gas mixture 1 or gas mixture 1' or a mixture of formed gas mixture 1' and remaining gas mixture 1, as a constituent of a gas mixture 2, to a heterogeneously catalyzed gas phase partial oxidation and/or partial gas phase ammoxidation of propylene present in gas mixture 1 and/or gas mixture 1' to obtain a gas mixture 3 comprising at least one target product P, d) removing target product from gas mixture 3 in at least one removal step and, of the remaining residual gas, recycling at least propane into the first reaction step, wherein
the prepurified propane is obtained from crude propane which comprises
$\geq$90% by weight of propane,
$\leq$99% by weight of propane and propylene, (frequently $\leq$98% by weight, or
$\leq$97% by weight, or $\leq$96% by weight, or $\leq$95% by weight),
$\geq$100 ppm by weight of $C_2$ hydrocarbons and
$\geq$100 ppm by weight of $C_4$ hydrocarbons,
with the proviso that the crude propane is conducted into a rectification column (generally having separating internals) and the purified propane is removed above the feed point with the proviso that the content of $C_2$ hydrocarbons based on propane present in % by weight in the purified propane is not less than 80% by weight of the corresponding content in the crude propane, and the content of $C_4$ hydrocarbons based on propane present in % by weight in the purified propane is at most 50% by weight of the corresponding content in the crude propane.

In general, the crude propane in the process according to the invention will comprise $\geq$200 ppm by weight of $C_2$ HC, frequently $\geq$300 ppm by weight of $C_2$ HC, in many cases $\geq$400 ppm by weight of $C_2$ HC, or $\geq$500 ppm by weight of $C_2$ HC, often $\geq$600 ppm by weight of $C_2$ HC, or $\geq$700 ppm by weight of $C_2$ HC and, if appropriate, $\geq$800 ppm by weight of $C_2$ HC, or $\geq$900 ppm by weight of $C_2$ HC, or $\geq$1000 ppm by weight of $C_2$ HC.

It will be appreciated that the crude propane in the process according to the invention may also comprise $\geq$1200 ppm by weight of $C_2$ HC, or $\geq$1400 ppm by weight of $C_2$ HC, or $\geq$1600 ppm by weight of $C_2$ HC, or $\geq$1800 ppm by weight of $C_2$ HC, or $\geq$2000 ppm by weight of $C_2$ HC. Possible contents of $C_2$ HC in crude propane to be used in accordance with the invention may also be $\geq$3000 ppm by weight, or $\geq$5000 ppm by weight, or $\geq$7000 ppm by weight, or else $\geq$10 000 ppm by weight. By definition, the content of $C_2$ HC in crude propane to be used in accordance with the invention is necessarily below 10% by weight, frequently at values of $\leq$8% by weight, in many cases at values of $\leq$7% by weight, or $\leq$6% by weight, or $\leq$5% by weight.

Normally at least 90% by weight, in many cases at least 92% by weight, or at least 94% by weight, or at least 96% by weight, or at least 98% by weight, or at least 99% by weight, of the content of $C_2$ HC in the crude propane is accounted for by ethane and ethylene. Based on the total amount of $C_2$ HC present in the crude propane, the acetylene content is frequently at values of $\leq$1% by weight, in many cases at values of $\leq$0.5% by weight, and often at values of $\leq$0.3% by weight, or $\leq$0.1% by weight.

Frequently, at least 50% by weight, in many cases at least 60% by weight, frequently at least 70% by weight, often at least 80% by weight and sometimes at least 90% by weight, of the total amount of $C_2$ HC present in the crude propane is accounted for by ethane.

However, the ethylene content of the crude propane can in many cases, based on the total amount of HC present, be up to 50% by weight.

In general, the crude propane in the process according to the invention will comprise $\geq$200 ppm by weight of $C_4$ HC, frequently $\geq$300 ppm by weight of $C_4$ HC, in many cases $\geq$400 ppm by weight of $C_4$ HC, or $\geq$500 ppm by weight of $C_4$ HC, often $\geq$600 ppm by weight of $C_4$ HC, or $\geq$700 ppm by weight of $C_4$ HC and, if appropriate, $\geq$800 ppm by weight of $C_4$ HC, or $\geq$900 ppm by weight of $C_4$ HC, or $\geq$1000 ppm by weight of $C_4$ HC.

It will be appreciated that the crude propane in the process according to the invention may also comprise $\geq$1200 ppm by weight of $C_4$ HC, or $\geq$1400 ppm by weight of $C_4$ HC, or $\geq$1600 ppm by weight of $C_4$ HC, or $\geq$1800 ppm by weight of $C_4$ HC, or $\geq$2000 ppm by weight of $C_4$ HC.

Possible contents of $C_4$ HC in crude propane to be used in accordance with the invention may also be $\geq$3000 ppm by weight, or $\geq$5000 ppm by weight, or $\geq$7000 ppm by weight, or else $\geq$10 000 ppm by weight. By definition, the content of $C_4$ HC in crude propane to be used in accordance with the invention is necessarily below 10% by weight, frequently at values of $\leq$8% by weight, in many cases at values of $\leq$7% by weight, or $\leq$6% by weight, or $\leq$5% by weight.

In numerous cases, at least 80% by weight, in many cases at least 90% by weight, or at least 92% by weight, or at least 94% by weight, or at least 96% by weight, of the content of $C_4$ HC in the crude propane is accounted for by butane (n-butane and isobutane). Of butane present in crude propane, generally $\geq$50% by weight, often $\geq$60% by weight, in many cases $\geq$70% by weight, is accounted for by isobutane. The n-butane content on the same basis is usually $\geq$10% by weight.

The total content of butenes, based on the total amount of $C_4$ HC present in the crude propane, is frequently at values of $\leq$1% by weight, in many cases at values of $\leq$0.5% by weight, and often at values of $\leq$0.3% by weight, or $\leq$0.1% by weight.

However, the crude propane normally comprises $\geq$10 ppm by weight of butenes.

When the crude propane also comprises hydrocarbons having five and more carbon atoms, they are removed together with the $C_4$ hydrocarbons in the inventive rectificative prepurification. In general, the total contents of $C_{\geq 5}$ HC in the crude propane is significantly below the $C_4$ content of the crude propane (normally less than 50% by weight of the $C_4$ HC content or even less). The same also applies to methane present, if appropriate, in the crude propane, except with the difference that its fate would substantially equate to that of the $C_2$ HC (i.e. the inventive $C_2$ HC outlet is generally correspondingly also the $C_1$ HC outlet).

Often, the total content of $C_{\geq 5}$ HC and methane (but also the two individual contents) in the crude propane are at values of $\leq$0.5% by weight, or $\leq$0.3% by weight, or $\leq$0.1% by weight.

Advantageously in accordance with the invention, the process according to the invention is carried out in such a way that the content based on the propane present of $C_4$ hydrocarbons in % by weight in the purified propane is at most 40% by weight, preferably at most 30% by weight, even better at most 20% by weight, more preferably at most 10% by weight and most preferably at most 5% by weight or at most 1% by weight, of the corresponding content in the crude propane.

Moreover, the process according to the invention is advantageously carried out in such a way that the content based on the propane present of $C_2$ hydrocarbons in % by weight in the purified propane is not less than 85% by weight, preferably not less than 90% by weight, more preferably not less than 95% by weight, even better not less than 100% by weight and most preferably more than 100% by weight (generally not more than 110% by weight and usually not more than 105% by weight), of the corresponding content in the crude propane. In other words, very particular preference is given to carrying out the process according to the invention in such a way that the purified propane comprises the $C_2$ hydrocarbons, based on the propane present therein, in enriched form in comparison to the content of $C_2$ hydrocarbons in the crude propane on the same basis. The inventive basis for the aforementioned is the already described natural outlet for $C_2$ HC in the inventive cycle method.

It is also favorable in accordance with the invention when the inventive rectificative prepurification of the crude propane is carried out in such a way that the prepurified propane withdrawn from the rectification column has a content both of isobutane and of total $C_4$ HC of $\leq 1000$ ppm by weight, or $\leq 900$ ppm by weight, or $\leq 800$ ppm by weight, or $\leq 700$ ppm by weight, or preferably $\leq 600$ ppm by weight, even better of $\leq 500$ ppm by weight, or $\leq 400$ ppm by weight, or $\leq 300$ ppm by weight, and even better $\leq 200$ ppm by weight. However, the content of isobutane in the propane prepurified in accordance with the invention will in many cases be $\geq 100$ ppm by weight.

Within the rectification column to be used for the inventive preremoval, descending liquid phase (reflux liquid) and ascending vapor phase are conducted in countercurrent relative to one another. Owing to the temperature and concentration gradients existing between the streams, heat and mass transfer takes place, which causes the desired separation. In general, the mass transfer surface is increased by separating internals in a rectification column. Useful such internals for the process according to the invention are in principle separating internals of any type. These may, for example, be structured packings, random packings and/or mass transfer trays of any type. Mass transfer trays on which there is equilibrium between descending liquid and ascending vapor are referred to as theoretical plates. This term can also be applied to all other separating internals suitable for countercurrent rectifications (for example structured packings and random packings). For convenience, this document therefore quite generally makes reference to theoretical plates. In this context, theoretical plate is defined as being that unit of space which brings about an enrichment or depletion in accordance with the thermodynamic equilibrium.

Separating internals preferred in accordance with the invention are mass transfer trays. Useful such mass transfer trays for the process according to the invention are sieve trays (for example those having forced liquid flow and those without forced liquid flow (for example all those described in DE-A 103 47 664)), and also, with particular preference, valve trays. In this document, valve trays shall be understood to mean crossflow trays which have tray drillholes having limited-stroke plate, ballast or lifting valves (floating flaps) which adjust the size of the vapor passage orifice to the particular column loading. The ascending gas stream is deflected, flows parallel to the tray into the accumulated reflux liquid and forms a froth layer. Drainpipes equipped with weirs conduct the reflux from tray to tray. Frequently, they have double-flow configuration. However, they may also have triple-flow and multiflow (for example four-flow) configuration.

The heat required for the inventive rectification is supplied appropriately, for example, via internal and/or external heat exchangers of conventional design and/or by means of jacket heating. Frequently, external circulation evaporators with natural or forced circulation are used.

The use of a plurality of evaporators connected in series or in parallel is possible in accordance with the invention. The heat carriers used may, for example, be steam which is normally obtained by the nature of the heat removal in the gas phase partial oxidation.

In general, the inventive objective in the context of the inventive prepurification of crude propane can be achieved by employing only one rectification column which has at least 5 theoretical plates, frequently at least 8 theoretical plates, in many cases at least 10 theoretical plates and often at least 14 theoretical plates. However, normally not more than 25 theoretical plates, frequently not more than 25 theoretical plates and in many cases not more than 21 theoretical plates will be required. In many cases, the number of theoretical plates will be from 15 to 20, for example 18.

Owing to the comparatively low number of plates required (when the crude propane comprises other $C_3$ HCs other than propane as constituents (e.g. propylene), there is substantially no separation among the $C_3$ HC in the context of the inventive prepurification; nor is such a separation required, since propylene is the desired reactant in gas mixture 2; cyclopropane is normally a constituent of crude propane in at best negligible amounts), the process according to the invention can be carried out without excessive construction complexity at top pressures (in the rectification column) of $\geq 5$ bar. In other words, inventive top pressures may be $\geq 7$ bar, or $\geq 9$ bar, or $\geq 11$ bar, or $\geq 13$ bar, or $\geq 15$ bar. However, the top pressure will normally be at values of $\leq 95$ bar, or $\leq 23$ bar, or $\leq 21$ bar.

Owing to the aforementioned pressure conditions, the temperature in the column bottom in the process according to the invention is normally at values of $\leq 100°$ C. Bottom temperatures favorable in accordance with the invention are from 40 to 90° C., preferably from 50 to 90° C. and more preferably from 60 to 80° C. Such comparatively low bottom temperatures enable a comparatively small extent of film formation and encrustation (fouling, polymers) in the bottom region.

The prepurified propane may be withdrawn either at the top of the rectification column or via side withdrawal from the rectification column. Frequently, this withdrawal is in liquid form (for example via a chimney tray). In the case of side withdrawal, typically at most up to another two theoretical plates are disposed above the withdrawal point.

Owing to the pressure conditions described, it is normally sufficient in the process according to the invention to cool the top condenser (which, inter alia, generates the reflux liquid) with water. Appropriately in accordance with the invention, this is an indirect tube bundle heat exchanger or a plate heat exchanger which is attached to the rectification column or may be integrated into the rectification column. Typically, the temperatures of the cooling water conducted through the rectification column (fed to the top condenser) are $\geq 0°$ C. and $\leq 40°$ C. In other words, typical cooling water temperatures are $\geq 5°$ C. and $\leq 35°$ C., or $\geq 10°$ C. and $\leq 30°$ C. Frequently, a cooling water temperature of 20° C. will be used.

In general, the top condenser has a vent which enables the least condensable constituents of the crude propane, for example $N_2$, $CO_2$ etc., to be discharged.

The ratio of the amount (kg/h) of reflux liquid recycled at the top of the column to the amount of crude propane fed into the rectification column will, in the inventive prepurification, typically be from 1 to 2.5, often from 1.5 to 2.5 and frequently from 1.5 to 2.0.

Particularly advantageously in accordance with the invention, the formation of the reflux liquid will be undertaken in such a way that a portion of the gas phase to be condensed for this purpose remains in gaseous form, so that the prepurified propane required in the first step can be fed thereto directly, withdrawn in gaseous form from the rectification column (gaseous top or side withdrawal).

In the process according to the invention, the crude propane will be fed into the rectification column, appropriately in accordance with the invention, in all cases in such a way that at least one theoretical plate is disposed above the feed point and at least one theoretical plate is disposed below the feed point. In general, the number of theoretical plates above the feed point ($Z_o$) should be greater than the number of theoretical plates below the feed point ($Z_u$).

Frequently, the ratio of $Z_o$ to $Z_u$ in the process according to the invention will be from 1.1 to 2, frequently from 1.1 to 1.5 and in many cases from 1.1 to 1.3.

The column bottoms consisting predominantly of $C_4$ HC (in particular n-butane and isobutane) is withdrawn continuously from the rectification column and, appropriately from an application point of view, is sent to a further utilization (for example synthesis gas production, partial oxidation, combustion). In the simplest way, this further utilization may, for example, be such that the bottoms liquid is sent as cofeed (to the paraffinic hydrocarbons) to a cracker (for example a steam cracker and/or a refinery cracker), in which thermal cracking of paraffinic hydrocarbons affords lower saturated and unsaturated hydrocarbons (for example $C_3$ and $C_4$ HC), and they are separated rectificatively in what are known as splitter columns (cf., for example, U.S. Pat. No. 3,392,216). When the bottoms liquid is utilized further in this way, the inventive rectificative preremoval may be carried out in a particularly simple manner with comparatively low definition, to the effect that the bottoms liquid still comprises up to 30% by weight of $C_3$ HC (normally, this $C_3$ HC content is $\leq 90$ or $\leq 10\%$ by weight). When alternative further utilizations are desired, the bottoms liquid will generally be more strongly depleted of $C_3$ HC. This depletion may, if appropriate, also be effected by rectificative treatment of the bottoms liquid in a second rectification column, as described, for example, in DE-A 24 13 463. This affords further prepurified propane useable in accordance with the invention.

Preference is given to manufacturing the rectification column to be used in accordance with the invention, including the preferred separating mass transfer trays, from stainless steel. Appropriately, the rectification column may be externally thermally insulated with materials such as glass or mineral wool, rigid foam, cork or Armaflex®, for example.

When the separating internals used in the rectification column are structured packings and/or random packings, they may consist, for example, of rings, spirals, saddles, Raschig, Intas or Pall rings, barrel or Intalox saddles, Top-Pak or braids. Of course, all of the possible column internals mentioned in this document may also be present in mixed form in the rectification column.

The pressure drop over the rectification column is normally at values of $\leq 1$ bar. Appropriately in accordance with the invention, the crude propane is fed into the rectification column in such a way that the crude propane is present in liquid form at least to an extent of 95% by weight, preferably to an extent of at least 97% by weight, or to an extent of at least 99% by weight. The temperature of the liquid crude propane may correspond to that temperature which exists within the rectification column at the feed point (the temperature may be controlled, for example, by heat exchange with the ambient air). It may also be below this temperature. Typically, the crude propane is fed into the rectification column, via a pressure reduction device (for example a throttle valve).

In general, the prepurified propane which is usable in accordance with the invention and is obtained in the inventive prepurification normally consists of propane, propylene, ethane and ethylene to an extent of at least 99% by weight, preferably to an extent of at least 99.5% by weight, more preferably to an extent of at least 99.7% by weight, most preferably to an extent of at least 99.9% by weight and most preferably to an extent of at least 99.95% by weight, or to an extent of at least 99.99% by weight. Typically, the $C_2$ HC content will be $\leq 5\%$ by weight, frequently $\leq 3\%$ by weight, in many cases $\leq 2\%$ by weight, often $\leq 1\%$ by weight and sometimes $\leq 0.5\%$ by weight (however, it will usually be $\geq 0.1\%$ by weight). In general, $\geq 50\%$ by weight, often $\geq 60\%$ by weight, frequently $\geq 80\%$ by weight, or $\geq 90\%$ by weight, or $\geq 95\%$ by weight, or $\geq 98\%$ by weight, or $\geq 99\%$ by weight thereof is accounted for by ethane.

This prepurified propane may subsequently be used appropriately. This may be done, for example, as described in the documents DE-A 102 45 585, DE-A 102 46 119, WO 01/96270, U.S. Pat. No. 3,161,670, DE-A 33 13 873, WO 01/96271, WO 03/011804, WO 03/076370, DE-A 103 16 039, DE-A 10 2004 032 129, EP-A 117 146, WO 04/031106, DE-A 103 16 039, DE-A 195 08 558, DE-A 198 37 520, DE-A 198 37 519, DE-A 198 37 517, WO 97/36849, EP-A 11 06 598, EP-A 274 681, EP-A 731 077, the German application DE-A 10 2005 009 885, the German application DE-A 10 2005 009 891 and DE-A 10 2004 003 212.

In this document, oxydehydrogenation of propane refers to a dehydrogenation which is forced by oxygen present and in which free hydrogen is neither formed as an intermediate nor is detectable. In contrast to the conventional dehydrogenation, which proceeds endothermically, the thermal character of the oxydehydrogenation is exothermic. The oxydehydrogenation of propane may be carried out under the action of elevated temperature, either under homogeneous (i.e. without the presence of a, for example, solid catalyst; cf., for example, U.S. Pat. No. 3,798,283) or heterogeneous catalysis (for example over solid catalysts; cf., for example, DE-A 20 58 054 and DE-A 195 30 494). Frequently, both reactions proceed in parallel. The same applies substantially to the conventional dehydrogenation, in which the dehydrogenation step is effected without active participation of oxygen (cf., for example, EP-A 731 077 and WO 01/96270). In other words, the primary by-product formed here is hydrogen and not water as in the case of the oxydehydrogenation. In a secondary reaction, the molecular hydrogen formed may of course be combusted partly or fully.

In this document, a full oxidation of propylene is understood to mean that the total amount of carbon present in the propylene is converted to oxides of carbon (CO, $CO_2$). All different reactions of propylene under the reactive action of molecular oxygen are summarized in this document by the term "partial oxidation". The additional reactive action of ammonia characterizes ammoxidation. In the case of skillful selection of the ammonia content, partial oxidation and ammoxidation proceed in a parallel, overlapping manner (cf., DE-A 102 45 585). The partial oxidation and/or ammoxidation products of propylene which are preferred in this document are acrolein, acrylic acid, propylene oxide and acrylonitrile.

As an oxidant, gas mixture 2 comprises molecular oxygen which may be present in gas mixture 2, for example, in pure form or in a mixture with gases which behave substantially inertly with regard to the partial oxidation/ammoxidation (for example in the form of air). Frequently, the reactants in gas mixture 2, also for reasons of heat removal and for reasons of safe reaction control, are diluted by at least one inert gas (e.g. $N_2$, $H_2O$, CO, $CO_2$, saturated hydrocarbons, for example $C_1$-$C_5$ (for example according to DE-A 19 24 431 and EP-A 293 224), He and/or Ar etc.).

All remarks in this document are applicable especially when the partial oxidation of the propylene present in gas mixture 2 is the partial oxidation of propylene to acrolein and acrylic acid.

In this case, gas mixture 2 advantageously has the following contents:

from 6 to 9% by volume of propylene, from 8 to 18% by volume of molecular oxygen, from 6 to 35% by volume of propane and from 32 to 72% by volume of molecular nitrogen.

The molar ratio $V_1$ of propane present in gas mixture 2 to propylene present in gas mixture 2 is, favorably in accordance with the invention, from 1 to 4. The molar ratio $V_2$ of molecular nitrogen present in gas mixture 2 to molecular oxygen present in gas mixture 2 is, appropriately in accordance with the invention, from 2 to 6. The molar ratio $V_3$ of molecular oxygen present in gas mixture 2 to propylene present in gas mixture 2 is, advantageously in accordance with the invention, from 1.3 to 2.4.

It is also known that it is generally favorable for the purpose of preventing undesired full combustion of propylene in the partial oxidation and/or ammoxidation when the propane content in gas mixture 2 is comparatively limited. Preferably in accordance with the invention, the propane content in gas mixture 2 is ≦60% by volume, or ≦50% by volume. Particularly favorable propane contents in gas mixture 2 are from 20 to 40% by volume, for example about 30% by volume.

When an ammonia content to be used if appropriate for nitrile generation is disregarded (i.e. it is also not taken into account in the reference basis for the percentages by volume), gas mixtures 2 suitable for the process according to the invention are generally those which comprise:

from 7 to 15% by volume of $O_2$, from 5 to 10% by volume of propylene, from 15 to 40% by volume of propane, frequently from 25 to 35% by volume, from 25 to 60% by volume of nitrogen, frequently from 40 to 60% by volume, from 1 to 5% by volume of CO, $CO_2$ and $H_2O$ and from 0 to 5% by volume of other constituents (e.g. $H_2$).

Otherwise, the process according to the invention may be carried out like the different basic variants described in the prior art (cf. in particular DE-A 102 45 585). In other words, in the simplest variant, all reaction steps of the process according to the invention are carried out in a (single) reaction zone and over a catalyst charge disposed therein, as described, for example, in EP-A 608 838, EP-A 529 853, DE-A 198 35 248, DE-A 101 45 958 and DE-A 101 45 958, and also DE-A 102 45 585 and the literature cited in these documents, using the example of the preparation of acrolein and/or acrylic acid.

Useful active compositions to be used for the catalyst charge are preferably multimetal oxides which comprise the following element combination in the stoichiometry I

$$Mo_1V_bM^1_cM^2_d \quad (I)$$

where $M^1$=Te and/or Sb, $M^2$=at least one of the elements from the group comprising Nb, Ta, W, Ti, Al, Zr, Cr, Mn, Ga, Fe, Ru, Co, Rh, Ni, Pd, Pt, La, Bi, Ce, Sn, Zn, Si, Na, Li, K, Mg, Ag, Au and In, b=from 0.01 to 1, c=from >0 to 1, and d=from >0 to 1 or consist of this element combination in oxidic form.

These are then in particular multimetal oxide active compositions of the general stoichiometry II

$$Mo_1V_bM^1_cM^2_dO_n \quad (II)$$

where the variables each have the definition detailed for the stoichiometry I and n=a number which is determined by the valency and frequency of the elements in (II) other than oxygen.

Preferably in accordance with the invention, $M^1$=Te and $M^2$=Nb, Ta, W and/or Ti.

Preferably, $M^2$=Nb. The stoichometric coefficient b is advantageously from 0.1 to 0.6. Correspondingly, the preferred range for the stoichiometric coefficient c ranges from 0.01 to 1 or from 0.05 to 0.4, and favorable values for d are from 0.01 to 1 or from 0.1 to 0.6.

The multimetal oxide active composition of the stoichiometry II preferably has the crystal structure and surface properties disclosed in DE-A 102 45 585. The multimetal oxide active compositions described may be used for the one-zone configuration of the process according to the invention (excluding the removal step) as such (i.e. in powder form) or shaped to suitable geometries (cf., for example, the coated catalysts of DE-A 100 51 419 and the geometric variants of DE-A 101 22 027). They are suitable in particular for the preparation of acrolein and/or acrylic acid, and also for preparing acryponitrile. The basis of this one-zone method is that the catalysts to be used are capable of catalyzing all reaction steps of the process according to the invention.

It is essential to the invention that, in the one-zone method described, ethane and ethylene are partially oxidized and/or ammoxidized in the inventive manner to acetonitrile, acetaldehyde and/or acetic acid.

The one-zone method described may be carried out either in a fixed catalyst bed or in a fluidized catalyst bed or moving bed. Corresponding process descriptions can be found in the documents of the prior art. When the process according to the invention is performed as a fixed bed reaction, for example for the preparation of acrylic acid in the one-zone method, it is appropriately carried out in a tube bundle reactor whose catalyst tubes are charged with the catalyst. Normally, a liquid is conducted around the catalyst tubes as a heat carrier, generally a salt melt. Alternatively, a thermoplate reactor may also be used, in which case the catalyst charge is disposed as a flat arrangement between cooling plates.

Viewed over the reactor, the reaction gas mixture is conducted within the catalyst tubes either in cocurrent or in countercurrent to the salt bath. The salt bath itself may perform a pure parallel flow relative to the catalyst tubes. It will be appreciated that this may also be superimposed with a crossflow. Overall, the salt bath may perform a meandering flow around the catalyst tubes, which is conducted in cocurrent or in countercurrent to the reaction gas mixture only when viewed over the reactor. Tube bundle reactors suitable for the process according to the invention are disclosed, for example, by the documents EP-A 700 714 and EP-A 700 893.

The different possible compositions of the starting reaction gas mixture for the one-zone variant of the process according to the invention may be taken from the prior art cited in connection with this process variant. For the preparation of acrylic acid, the composition of the starting reaction gas mixture typically varies within the following range (molar ratios):

propane:oxygen::$H_2O$:other constituents (in particular inert diluent gases)=

1:(0.1-10):(>0-50):(>0-50).

The aforementioned ratio is preferably

1:(0.5-5):(1-30):(1-30).

The aforementioned ranges apply especially when the other constituents used are predominantly molecular nitrogen. The reaction temperature is typically is from 250 to 550° C. (the conditions for the ammoxidation are comparable, disregarding the fact that the reaction gas mixture additionally comprises ammonia (cf., for example, EP-A 529 853)).

In the one-zone variant of the process according to the invention, the hourly space velocity on the fixed catalyst bed charge with propane may, for example, be from 10 to 500 l (STP)/l (fixed bed)·h. The hourly space velocity with starting reaction gas mixture is frequently in the range from 100 to 10 000 l (STP)/l·h, in many cases in the range from 500 to 5000 l (STP)/l·h.

The multimetal oxide active compositions recommended for the one-zone method may of course also be used in the process according to the invention in a form diluted with finely divided, for example colloidal, materials such as silicon dioxide, titanium dioxide, aluminum oxide, zirconium oxide and niobium oxide.

The dilution mass ratio may be up to 9 (diluent):1 (active composition). In other words, possible diluent mass ratios are, for example, 6 (diluent):1 (active composition) and 3 (diluent):1 (active composition). The diluents can be incorporated according to DE-A 101 22 027, before or after the calcination. It will be appreciated that it is also possible to use other catalyst systems for the inventive one-zone method, as described, for example, by JP-A 3-170445. When the process according to the invention is realized in one reaction zone, one of the possible cases is that in which gas mixture 1 and gas mixture 1 are identical.

Preference is given in accordance with the invention to realizing the process according to the invention in more than reaction zone, as described, for example, by EP-A 938463, EP-A 117146, DE-A 3313573, GB-A 2118939, U.S. Pat. No. 3,161,670, WO 01/96270, EP-A 731077, DE-A 19837520, DE-A 19837517, DE-A 19837519, DE-A 19837518, DE-A 19837520, DE-A 10131297 and DE-A 10211275.

More than one reaction zone means primarily that at least one reaction step of the process according to the invention is carried out under conditions which can be selected at least partly independently of those of the at least one other reaction step within the process according to the invention, or, although only secondarily, that at least partly independent reaction conditions can be realized within one and the same reaction step along the reaction path (the latter is the case, for example, when so-called multizone methods (with independently adjustable temperature zones) are employed for one reaction step, as described, for example, by DE-A 19948241, DE-A 19927624, DE-A 19910508, DE-A 19910506 and DE-A 19948248). In other words, when the process according to the invention comprises, for example two reaction steps, it would be possible to use, for example, a different catalyst or a different catalyst charge to that for the second reaction step. Or, the procedure could be, in the case of use of identical catalysts or catalyst charges for both reaction steps, to select and adjust the reaction temperatures for the two reaction steps independently of one another. Of course, both can also be employed superimposed on one another.

The basis of the advantage of the multizone method is that it in principle enables improved adjustment of the reaction conditions to the requirements of the individual reaction steps of the process according to the invention.

This advantage is well known of the heterogeneously catalyzed gas phase partial oxidation of propylene to acrylic acid with molecular oxygen.

It proceeds along the reaction coordinate in principle in two steps successive along their reaction coordinate, of which the first leads to acrolein and the second from acrolein to acrylic acid.

This reaction sequence in a manner known per se opens up the possibility of implementing the partial oxidation according to the invention of the propylene present in gas mixture 2 in two oxidation zones arranged in series, in which case the oxidic catalyst to be used in each of the two oxidation zones can be optimized (this optimization opportunity also permits the partial oxidation of the propylene to be stopped at acrolein and the acrolein to be isolated). For instance, the preferred catalyst for the first oxidation zone (propylene→acrolein) is generally based on multimetal oxides comprising the element combination Mo—Bi—Fe, while the catalyst preferred for the second oxidation zone (acrolein→acrylic acid) is normally based on multimetal oxides comprising the element combination Mo—V (for example also those which have been recommended in this document for the one-zone method). However, these two reaction steps may in principle also be carried out in a single reaction zone and over a single catalyst.

Quite generally, the first reaction step in the process according to the invention will appropriately be carried out in a separate reaction zone.

In the case of an oxydehydrogenation of propane, this may be carried out in the gas phase as a homogeneously and/or heterogeneously catalyzed oxydehydrogenation of propane to propylene using molecular oxygen. The source of the molecular oxygen used may be air, pure molecular oxygen or air enriched with molecular oxygen (the oxydehydrogenation is normally accompanied by a partial oxidation of the $C_2$ HC; this facilitates an appropriate outlet downstream of the oxydehydrogenation).

When the reaction zone is configured as a homogeneous-oxydehydrogenation, this can in principle be carried out in such a way as described, for example, in the documents U.S. Pat. No. 3,798,283, CN-A 1 105 352, Applied Catalysis, 70(2) 1991, p. 175-187, Catalysis Today 13, 1992, p. 673-678 and in the application DE-A 19 622 331. An appropriate oxygen source is air. The temperature of the homogeneous oxydehydrogenation is advantageously selected within the range from 300 to 700° C., preferably within the range from 400 to 600° C., more preferably within the range from 400 to 500° C. The working pressure may be from 0.5 to 100 bar, in particular from 1 to 10 bar. The residence time is typically from 0.1 or 0.5 to 20 seconds, preferably from 0.1 or 0.5 to 5 seconds.

The reactor used may be, for example, a tube furnace or a tube bundle reactor, for example a countercurrent tube furnace using flue gas as the heat carrier or a tube bundle reactor using a salt melt as the heat carrier. The propane to oxygen ratio in the starting mixture is preferably from 0.5:1 to 40:1, in particular between 1:1 and 6:1, more preferably between 2:1 and 5:1. The starting mixture may also comprise further, preferably inert (in this document, inert constituents are preferably understood quite generally to mean those constituents which are converted in the relevant reaction step to an extent of less than 5 mol %, preferably to an extent of less than 3 mol % and more preferably to an extent of less than 1 mol %; most preferably, they do not react at all), constituents such as water, carbon dioxide, carbon monoxide, nitrogen, noble gases, other hydrocarbons (e.g. secondary components present in the crude propane), and/or propylene, etc., also including recycled (cycle gas) constituents.

When the propane dehydrogenation is configured as a heterogeneously catalyzed oxydehydrogenation, this can in principle be carried out as described, for example, in the documents U.S. Pat. No. 4,788,371, CN-A 1073893, Catalysis Letters 23 (1994), 103-106, W. Zhang, Gaodeng Xuexiao Huaxue Xuebao, 14 (1993) 566, Z. Huang, Shiyou Huagong, 21 (1992) 592, WO 97/36849, DE-A 197 53 817, U.S. Pat. No. 3,862,256, U.S. Pat. No. 3,887,631, DE-A 195 30 454, U.S. Pat. No. 4,341,664, J. of Catalysis 167, 560-569 (1997), J. of Catalysis 167, 550-559 (1997), Topics in Catalysis 3 (1996) 265-275, U.S. Pat. No. 5,086,032, Catalysis Letters 10 (1991), 181-192, Ind. Eng. Chem. Res. 1996, 35, 14-18, U.S. Pat. No. 4,255,284, Applied Catalysis A: General, 100 (1993), 111-130, J. of Catalysis 148, 56-67 (1994), V. Cortés Corberán and S. Vic Bellón (Ed.), New Developments in Selective Oxidation II, 1994, Elsevier Science B.V., P. 305-313, 3$^{rd}$ World Congress on Oxidation Catalysis, R. K. Grasselli, S. T. Oyama, A. M. Gaffney and J. E. Lyons (Ed.), 1997, Elsevier Science B.V., p. 375 ff. or in DE-A 198 37 520, DE-A 198 37 517, DE-A 198 37 519 and DE-A 198 37 518. The oxygen source used may also be air. However, the oxygen source consists frequently of at least 90 mol % of molecular oxygen, and in many cases at least 95 mol % of oxygen.

The catalysts suitable for the heterogeneously catalyzed oxydehydrogenation are not subject to any particular restrictions. Suitable catalysts are any oxydehydrogenation catalysts known to those skilled in the art which are capable of oxidizing propane to propylene. In particular, any oxydehydrogenation catalysts specified in the documents cited above may be used. Examples of suitable catalysts include oxydehydrogenation catalysts which comprise the MoVNb oxides or vanadyl pyrophosphate, if appropriate with promoter. An example of such an advantageous oxydehydrogenation catalyst is a catalyst as also recommended for the one-zone method which comprises a mixed metal oxide comprising Mo, V, Te, O and X as essential constituents where X is at least one element selected from niobium, tantalum, tungsten, titanium, aluminum, zirconium, chromium, manganese, gallium, iron, ruthenium, cobalt, rhodium, nickel, palladium, platinum, antimony, bismuth, boron, indium, silicon, lanthanum, sodium, lithium, potassium, magnesium, silver, gold and cerium (on this subject, see also EP-A 938463 and EP-A 167109). Further particularly suitable oxydehydrogenation catalysts are the multimetal oxide compositions or catalysts A of DE-A-197 53 817 and the catalysts of DE-A 19838312, and the multimetal oxide compositions or catalysts A in the former document mentioned as being preferable are very particularly advantageous. In other words, useful active compositions are in particular multimetal oxide compositions of the general formula III

$$M^1_a Mo_{1-b} M^2_b O_x \quad (III)$$

where
M$^1$=Co, Ni, Mg, Zn, Mn and/or Cu,
M$^2$=W, V, Te, Nb, P, Cr, Fe, Sb, Ce, Sn and/or La,
a=0.5-1.5
b=0-0.5
and
x=a number which is determined by the valency and frequency of the elements in (III) other than oxygen. They can be prepared and shaped as described in DE-A 102 45 585.

For the heterogeneously catalyzed oxydehydrogenation of propane, the reaction temperature is preferably in the range from 200 to 600° C., in particular in the range from 250 to 500° C., more preferably in the range from 350 to 440° C. The working pressure is preferably in the range from 0.5 to 10 bar, in particular from 1 to 10 bar, more preferably from 1 to 5 bar. Working pressures of above 1 bar, for example from 1.5 to 10 bar, have been found to be particularly advantageous. In general, heterogeneously catalyzed oxydehydrogenation of propane is effected over a fixed catalyst bed. The latter is appropriately charged into the tubes of a tube bundle reactor, as described, for example, in EP-A-0 700 893 and EP-A-0 700 714 and also in the literature cited in these documents. The average residence time of the reaction gas mixture in the catalyst bed is appropriately from 0.5 to 20 seconds. The ratio of propane to oxygen varies with the desired conversion and selectivity of the catalyst, and is advantageously in the range from 0.5:1 to 40:1, in particular from 1:1 to 6:1, more preferably from 2:1 to 5:1. In general, the propylene selectivity falls with rising propane conversion. The propane to propylene reaction is therefore preferably carried out in such a way that relatively low conversions of propane are achieved at high selectivities for propylene. The conversion of propane is more preferably in the range from 5 to 40 mol %, frequently in the range from 10 to 30 mol %. In this connection, the term "propane conversion" means the proportion of propane fed (sum of propane which is present in the prepurified propane and cycle gas recycled if appropriate, and is converted in single pass). In general, the selectivity of the propylene formation is from 50 to 98 mol %, more preferably from 80 to 98 mol %, where the term "selectivity" refers to the moles of propylene generated per mole of reacted propane, expressed as a molar percentage.

In general, the starting mixture used in the oxidative propane dehydrogenation comprises from 5 to 95 mol % of propane (based on 100 mol % of starting mixture). In addition to propane and oxygen, the starting mixture for the heterogeneously catalyzed oxydehydrogenation may also comprise further, in particular inert, constituents such as carbon dioxide, carbon monoxide, nitrogen, noble gases, other hydrocarbons, e.g. secondary components present in the crude propane, and/or propylene. The heterogeneous oxydehydrogenation may also be carried out in the presence of diluents, for example steam.

Any desired reactor sequence known to those skilled in the art may be used for carrying out the homogeneous oxydehydrogenation or the heterogeneously catalyzed oxydehydrogenation of propane. For example, the oxydehydrogenation may be carried out in a single reactor or in a battery of two or more reactors, between which oxygen is optionally introduced. The possibility also exists of practicing the homogeneous and the heterogeneously catalyzed oxydehydrogenation combined with each other.

In general, the propane dehydrogenation in the first reaction zone may also be carried out as a heterogeneously catalyzed propane dehydrogenation with substantial exclusion of oxygen as described in DE-A 3313573, WO 01/96270, DE-A 10131297 or DE-A 10211275, or as follows.

Since the heterogeneously catalyzed dehydrogenation reaction proceeds with increasing volume, the conversion may be increased by reducing the partial pressure of the products. This can be achieved in a simple manner, for example by dehydrogenating at reduced pressure and/or by admixing substantially inert diluent gases, for example steam, which normally constitutes an inert gas for the dehydrogenation reaction. The addition of water can preferably also serve in particular to protect those parts of the reaction apparatus which are in contact with highly reducing atmosphere (in particular at high temperature) from corrosive damage, for example by "metal dusting". Dilution with steam generally results in the further advantage of reduced carbonization of the catalyst used, since the steam reacts by the principle of coal gasification with carbon formed. Also, steam may be used as a diluent gas in the subsequent at least one partial oxidation and/or ammoxidation zone (also referred to in this document for short as at least one partial zone). However, steam may also be partially or completely removed from the dehydrogenation product mixture in a simple manner (for example by condensing), which opens up the possibility of increasing the proportion of the diluent gas N$_2$ in the further use of the modified product mixture obtained in this way in the at least one partial zone. Examples of further suitable diluents for the heterogeneously catalyzed propane dehydrogenation include CO, methane, ethane, $CO_2$, nitrogen and noble gases such as He, Ne and Ar. All diluents specified may be used either alone or in the form of a wide variety of mixtures. It is advantageous that the diluents specified are generally also suitable diluents in the at least one partial zone. Generally, as already stated, preference is given to diluents which behave inertly in the particular reaction zone (i.e. which change chemically to an extent of less than 5 mol %, preferably to an extent of less than 3 mol % and even better to an extent of less than 1 mol %). In principle, useful catalysts for the heterogeneously catalyzed propane dehydrogenation are all dehydrogenation catalysts known from the prior art. They can be roughly divided into two groups, i.e. into those which are of an oxidic nature (for example chromium oxide and/or aluminum oxide) and into those which consist of at least one generally comparatively noble metal (for example platinum) deposited on a generally oxidic support.

Some of the dehydrogenation catalysts which can be used are all those recommended in WO 01/96270, EP-A 731077, DE-A 10211275, DE-A 101 31 297, WO 99/46039, U.S. Pat. No. 4,788,371, EP-A-0 705 136, WO 99/29420, U.S. Pat. No. 4,220,091, U.S. Pat. No. 5,430,220, U.S. Pat. No. 5,877,369, EP-A-0 117 146, DE-A 199 37 196, DE-A 199 37 105 and DE-A 199 37 107. In particular, the catalyst of Example 1, Example 2, Example 3 and Example 4 of DE-A 199 37 107 may be used.

These are dehydrogenation catalysts which comprise from 10 to 99.9% by weight of zirconium dioxide, from 0 to 60% by weight of aluminum oxide, silicon dioxide and/or titanium dioxide and from 0.1 to 10% by weight of at least one element of the first or second main group, of an element of the third transition group, of an element of the eighth transition group of the Periodic Table, lanthanum and/or tin, with the proviso that the sum of the percentages by weight is 100% by weight.

To carry out the heterogeneously catalyzed propane dehydrogenation, useful reactor types and process variants are all of those known from the prior art. Descriptions of such process variants are present, for example, in all prior art documents cited in relation to the dehydrogenation catalysts and also in relation to the appropriate use of the prepurified propane.

A comparatively comprehensive description of dehydrogenation processes suitable according to the invention is also contained in "Catalytica® Studies Division, Oxidative Dehydrogenation and Alternative Dehydrogenation Processes", Study Number 4192 OD, 1993, 430 Ferguson Drive, Mountain View, Calif., 94043-5272 U.S.A.

It is characteristic of the partial heterogeneously catalyzed dehydrogenation of propane that it proceeds endothermically. This means that the heat (energy) required for the attainment of the necessary reaction temperature has to be supplied to the starting reaction gas mixture either beforehand and/or in the course of the heterogeneously catalyzed dehydrogenation.

Owing to the high reaction temperatures required, it is further typical, especially for heterogeneously catalyzed dehydrogenations of propane, that small amounts of high-boiling high molecular weight organic compounds, up to and including carbon, are formed which deposit on the catalyst surface and thus deactivate it. In order to minimize this disadvantageous accompanying phenomenon, the propane-containing reaction gas mixture to be passed over the catalyst surface at an elevated temperature for heterogeneously catalyzed dehydrogenation may be diluted with steam. Carbon which is deposited is partly or fully eliminated under the resulting conditions by the principle of coal gasification.

Another means of eliminating deposited carbon compounds involves allowing an oxygen-containing gas to flow through the dehydrogenation catalyst at elevated temperature from time to time and thus to effectively burn off the deposited carbon. However, a substantial suppression of formation of carbon deposits is also possible by adding molecular hydrogen to the propane to be dehydrogenated with heterogeneous catalysis before it is conducted over the dehydrogenation catalyst at elevated temperature.

It will be appreciated that the possibility also exists of adding steam and molecular hydrogen in a mixture to the propane to be dehydrogenated with heterogeneous catalysis. Addition of molecular hydrogen to the heterogeneously catalyzed dehydrogenation of propane also reduces the undesired formation of allene (propadiene), propyne and acetylene as by-products.

It may therefore be appropriate in accordance with the invention to carry out the propane dehydrogenation (e.g. with comparatively low propane conversion) (quasi-) adiabatically. This means that the starting reaction gas mixture will generally initially be heated to a temperature of from 500 to 700° C. (or from 550 to 650° C.) (for example by direct firing of the wall surrounding it). Normally, a single adiabatic pass through a catalyst bed will then be sufficient in order to achieve the desired conversion, and the reaction gas mixture will cool by from about 30° C. to 200° C. (depending on conversion and dilution). Presence of steam as a heat carrier is also noticeably advantageous from the point of view of an adiabatic method. The lower reaction temperature allows longer lifetimes of the catalyst bed used.

In principle, the heterogeneously catalyzed propane dehydrogenation with comparatively low propane conversion, whether conducted adiabatically or isothermally, can be carried out either in a fixed bed reactor or else in a moving bed or fluidized bed reactor.

Remarkably, to realize the process according to the invention, especially in adiabatic operation, a single shaft furnace reactor which is flowed through by the reaction gas mixture axially and/or radially is sufficient as a fixed bed reactor.

In the simplest case, this is a single closed reaction volume, for example a vessel, whose internal diameter is from 0.1 to 10 m, possibly also from 0.5 to 5 m, and in which the fixed catalyst bed is applied to a support device (for example a grid). The reaction volume which is charged with catalyst and heat-insulated in adiabatic operation is flowed through axially by the hot, propane-containing reaction gas. The catalyst geometry may be either spherical or else annular or strand-shaped. Since the reaction volume can be realized in this case by a very inexpensive apparatus, preference is given to all catalyst geometries which have a particularly low pressure drop. These are in particular catalyst geometries which lead to a large cavity volume or are structured, for example monoliths or honeycombs. To realize a radial flow of the propane-containing reaction gas, the reactor may, for example, consist of two concentric cylindrical grids disposed in a shell and the catalyst bed may be arranged in the annular gap. In the adiabatic case, the metal shell would in turn be thermally insulated.

Useful catalyst charges for a heterogeneously catalyzed propane dehydrogenation with comparatively low propane conversion on a single pass are in particular the catalysts disclosed in DE-A 199 37 107, in particular all of those disclosed by way of example.

After a prolonged operating time, the aforementioned catalysts can be regenerated in a simple manner, for example by initially passing air (preferably) diluted with nitrogen and/or steam in first regeneration stages over the catalyst bed at an entrance temperature of from 300 to 600° C., frequently from 400 to 550° C. The catalyst hourly space velocity of regeneration gas may be, for example, from 50 to 10 000 $h^{-1}$ and the oxygen content of regeneration gas may be from 0.5 to 20% by volume.

In subsequent further regeneration stages, the regenerating gas used under otherwise identical regeneration conditions may be air. From an application point of view, it is advantageous to flush the catalyst with inert gas (for example $N_2$) before its regeneration.

It is generally advisable to subsequently regenerate with pure molecular hydrogen or with molecular hydrogen diluted with inert gas (preferably steam) (the hydrogen content should be $\geq$1% by volume) under otherwise identical conditions.

The heterogeneously catalyzed propane dehydrogenation with comparatively low propane conversion ($\leq$30 mol %) may in all cases be carried out at the same catalyst hourly space velocities (with regard both to the reaction gas overall and to the propane present therein) as the variants with high propane conversion ($\geq$30 mol %). This hourly space velocity of reaction gas may be, for example, from 100 to 10 000 $h^{-1}$, frequently from 300 to 5000 $h^{-1}$, i.e. in many cases from about 500 to 3000 $h^{-1}$.

In a particularly elegant manner, the heterogeneously catalyzed propane dehydrogenation (in particular at low propane conversion) can be realized in a tray reactor.

This comprises more than one catalyst bed catalyzing the dehydrogenation in spatial succession. The catalyst bed number may be from 1 to 20, advantageously from 2 to 8, or else from 3 to 6. The catalyst beds are preferably arranged in radial or axial succession. From an application point of view, it is advantageous to use the fixed bed catalyst type in such a tray reactor.

In the simplest case, the fixed catalyst beds in a shaft furnace reactor are arranged axially or in the annular gaps of concentric cylindrical grids. However, it is also possible to arrange the annular gaps in segments above one another and to conduct the gas after passing radially through one segment into the next segment above it or below it.

Appropriately, the reaction gas mixture will be subjected to intermediate heating in the tray reactor on its way from one catalyst bed to the next catalyst bed, for example by passing it over heat exchanger ribs heated by hot gases or by passing it through pipes heated by hot combustion gases.

When the tray reactor is otherwise operated adiabatically, it is sufficient for propane conversions of $\leq$30 mol %, especially when using the catalysts described in DE-A 199 37 107, especially those of the exemplary embodiments, to conduct the reaction gas mixture into the dehydrogenation reactor preheated to a temperature of from 450 to 550° C. and to keep it within this temperature range inside the tray reactor. This means that the entire propane dehydrogenation can thus be realized at very low temperatures, which is particularly advantageous for the lifetime of the fixed catalyst beds between two regenerations.

It is even more beneficial to carry out the catalytic dehydrogenation, i.e., for example, the above-outlined intermediate heating, in a direct way (autothermal method). To this end, a limited amount of molecular oxygen is added to the reaction gas mixture either before it flows through the first catalyst bed and/or between the subsequent catalyst beds. Depending on the dehydrogenation catalyst used, a limited combustion of the hydrocarbons contained in the reaction gas mixture (generally accompanied by a partial oxidation of $C_2$ HC), any coke or coke-like compounds already deposited on the catalyst surface and/or hydrogen formed in the course of the heterogeneously catalyzed propane dehydrogenation and/or added to the reaction mixture is thus effected (it may also be advantageous from an application point of view to introduce catalyst beds in the tray reactor which are charged with catalysts which specifically (selectively) catalyze the combustion of hydrogen (and/or of hydrocarbon) (examples of useful catalysts include those of the documents U.S. Pat. No. 4,788,371, U.S. Pat. No. 4,886,928, U.S. Pat. No. 5,430,209, U.S. Pat. No. 5,530,171, U.S. Pat. No. 5,527,979 and U.S. Pat. No. 5,563,314; for example, such catalyst beds may be accommodated in the tray reactor in alternation to the beds comprising dehydrogenation catalysts)). The heat of reaction released thus allows virtually isothermal operation of the heterogeneously catalyzed propane dehydrogenation in a quasi-autothermal manner. As the selected residence time of the reaction gas in the catalyst bed is increased, propane dehydrogenation is thus possible at decreasing or substantially constant temperature, which allows particularly long lifetimes between regenerations.

In general, oxygen feeding as described above should be carried out in such a manner that the oxygen content of the reaction gas mixture, based on the amount of propane and propylene contained therein, is from 0.5 to 30% by volume. Useful oxygen sources include both pure molecular oxygen and oxygen diluted with inert gas, for example CO, $CO_2$, $N_2$ or noble gases, but in particular also air. The resulting combustion gases generally have an additional dilution effect and thus support heterogeneously catalyzed propane dehydrogenation.

The isothermicity of the heterogeneously catalyzed propane dehydrogenation can be further improved by incorporating closed (for example tubular) internals which have advantageously, but not necessarily, been evacuated before filling in the spaces between the catalyst beds in the tray reactor. Such internals may also be placed in each catalyst bed. These internals contain suitable solids or liquids which evaporate or melt above a certain temperature, thus consuming heat, and, where the temperature falls below this value, condense again and thus release heat.

One method of heating the starting reaction gas mixture for the heterogeneously catalyzed propane dehydrogenation to the required reaction temperature involves combusting a portion of the propane and/or $H_2$ contained therein by means of molecular oxygen (for example over suitable specific combustion catalysts, for example by simply passing over and/or through) and to effect the heating to the desired reaction temperature by means of the heat of combustion released in this manner (this is generally likewise accompanied by a partial oxidation of $C_2$ HC). The resulting combustion products, such as $CO_2$ and $H_2O$, and also any $N_2$ accompanying the molecular oxygen required for the combustion advantageously constitute inert diluent gases.

The abovementioned hydrogen combustion can be particularly elegantly realized as described in DE-A 102 11 275. This is a process for continuously partially dehydrogenating propane in the gas phase under heterogeneous catalysis by continuously feeding a reaction gas comprising the propane to be dehydrogenated to a reaction zone, conducting the reaction gas in the reaction zone over at least one fixed catalyst bed, over which molecular hydrogen and at least partially propylene are formed by catalytic dehydrogenation, adding at least one molecular oxygen-containing gas to the reaction gas before and/or after entry into the reaction zone, partially oxidizing the molecular oxygen in the molecular hydrogen contained in the reaction gas in the reaction zone to give steam and withdrawing a product gas from the reaction zone which comprises molecular hydrogen, steam, propylene and propane, which comprises dividing the product gas removed from the reaction zone into two portions of identical composition and recycling one of the two portions into the dehydrogenation reaction zone as cycle gas and further using the other portion as gas mixture 1 in accordance with the invention.

In principle, it is also possible in a tray reactor to carry out a combination of heterogeneously catalyzed oxidative and classical dehydrogenation. For example, every second catalyst bed can be charged with an oxydehydrogenation catalyst and the other catalyst beds with a classical dehydrogenation catalyst. Between the beds, oxygen is fed intermediately. The exothermic oxydehydrogenation can then be utilized alternatively for hydrogen combustion, in order to heat the reaction mixture.

Following the documents EP-A 117 146, DE-A 33 13 573 and U.S. Pat. No. 3,161,670, gas mixture 1 may be used as such to obtain gas mixture 2. If required, it is also possible to partly remove constituents other than propane and propylene from gas mixture 1 before it is used to obtain gas mixture 2. The latter may be effected, for example, by passing gas mixture 1, if appropriate after it has been cooled beforehand in an indirect heat exchanger, through a membrane, generally configured as a tube, which is permeable only to molecular hydrogen. The molecular hydrogen removed in this way may, if required, be recycled partly into the heterogeneously catalyzed dehydrogenation of propane or be sent to another use. It is also possible to remove a portion or the entirety of steam present in gas mixture 1 from gas mixture 1 before gas mixture 1 is used to obtain gas mixture 2.

Alternatively, the preferably cooled (preferably to temperatures of from 10 to 70° C.) gas mixture 1, for example at a pressure of from 0.1 to 50 atm and a temperature of from 0 to 100° C., can be contacted with (for example by simply passing it through) a (preferably high-boiling) organic solvent (preferably hydrophobic), in which propane and propene are preferentially absorbed. Subsequent desorption, rectification and/or stripping with a gas which behaves inertly with regard to the heterogeneously catalyzed gas phase partial oxidation and/or ammoxidation and/or is required as a reactant in this reaction zone (for example air) recovers a mixture of propane and propene in purified form which are used to obtain gas mixture 2 (in the case of stripping with air, the gas mixture 1' obtained may be identical to gas mixture 2, i.e. can be used directly as such to charge the heterogeneously catalyzed gas phase partial oxidation and/or ammoxidation). As an alternative to the described separating step via absorption, a pressure swing absorption or a pressure rectification are also useful. Although it is always possible for a $C_2$ outlet to be associated with aforementioned separating steps, the outlet can be kept substantially simpler owing to the inventive $C_2$ reactive outlet.

Useful absorbents for the absorptive removal described above are in principle any absorbents which are capable of absorbing propane and propene. The absorbent is preferably an organic solvent which is preferably hydrophobic and/or high-boiling. Advantageously, this solvent has a boiling point (at an atmospheric pressure of 1 atm) of at least 120° C., preferably of at least 180° C., more preferably from 200 to 350° C., in particular from 250 to 300° C., with greater preference from 260 to 290° C. Appropriately, the flashpoint (at an atmospheric pressure of 1 atm) is above 110° C. In general, suitable absorbents include relatively nonpolar organic solvents, for example aliphatic hydrocarbons, which preferably comprise no externally active polar groups, but also aromatic hydrocarbons. In general, it is desirable that the absorbent has a very high boiling point and at the same time very high solubility for propane and propene.

Examples of useful absorbents include aliphatic hydrocarbons, for example $C_8$-$C_{20}$-alkanes or -alkenes, or aromatic hydrocarbons, for example middle oil fractions from paraffin distillation, or ethers having bulky (sterically demanding) groups on the oxygen atom, or mixtures thereof, to which a polar solvent, for example the 1,2-dimethyl phthalate disclosed in DE-A 43 08 087, may be added. Further suitable absorbents include esters of benzoic acid and phthalic acid with straight-chain alkanols comprising from 1 to 8 carbon atoms, such as n-butyl benzoate, methyl benzoate, ethyl benzoate, dimethyl phthalate and diethyl phthalate, and also heat carrier oils such as diphenyl, diphenyl ether and mixtures of diphenyl and diphenyl ether or chlorine derivatives thereof, and triarylalkenes, for example 4-methyl-4'-benzyldiphenylmethane and its isomers 2-methyl-2'-benzyldiphenylmethane, 2-methyl-4'-benzyldiphenylmethane and 4-methyl-2'-benzyldiphenylmethane and mixtures of such isomers. A useful absorbent is a solvent mixture of diphenyl and diphenyl ether, preferably in the azeotropic composition, in particular of about 25% by weight of diphenyl (biphenyl) and about 75% by weight of diphenyl ether, for example the commercially obtainable Diphyl® (for example obtained from Bayer Aktiengesellschaft). Frequently, this solvent mixture comprises a solvent such as dimethyl phthalate in an amount of from 0.1 to 25% by weight, based on the entire solvent mixture. Particularly useful absorbents also include octanes, nonanes, decanes, undecanes, dodecanes, tridecanes, tetradecanes, pentadecanes, hexadecanes, heptadecanes and octadecanes, and tetradecanes in particular have been found to be particularly useful. It is favorable when the absorbent used on the one hand attains the abovementioned boiling point and on the other hand at the same time does not have too high a molecular weight. Advantageously, the molecular weight of the absorbent is $\leq 300$ g/mol. The paraffin oils having from 8 to 6 carbon atoms described in DE-A 33 13 573 are likewise suitable. Examples of useful trade products include the products sold by Haltermann including Halpasols i, for example Halpasol 250/340 i and Halpasol 250/275 i, and also printing ink distillates sold as PKWF and Printosol. Preference is given to aromatic-free commercial products, e.g. those of the PKWFaf type. Further suitable commercial products are n-paraffin ($C_{13}$-$C_{17}$) or Mihagol® 5 from Erdöl-Raffinerie-Emsland GmbH, LINPAR® 14-17 from CONDEA Augusta S.p.A. (Italy) or SASOL Italy S.p.A., normal paraffins (heavy) $C_{14}$-$C_{18}$ from SLOVNAFT in Slovakia.

The contents (reported in area percent of gas chromatography analysis) in the aforementioned products of linear hydrocarbons are typically:

total $C_9$ to $C_{13}$: less than 1%; $C_{14}$: 30 to 40%; $C_{15}$: 20 to 33%; $C_{16}$: 18 to 26%; $C_{17}$: up to 18%; $C_{\geq 18}$: $\leq 2\%$.

A typical composition of the product from SASOL is:

$C_{13}$: 0.48%; $C_{14}$: 39.8%; $C_{15}$: 20.8%; $C_{16}$: 18.9%; $C_{17}$: 17.3%; $C_{18}$: 0.91%; $C_{19}$: 0.21%.

A typical composition of the product from Haltermann is:

$C_{13}$: 0.58%; $C_{14}$: 33.4%; $C_{15}$: 32.8%; $C_{16}$: 25.5%; $C_{17}$: 6.8%; $C_{\geq 18}$: <0.2%.

The performance of the absorption is not subject to any particular restrictions. All processes and conditions familiar to those skilled in the art may be used, as have already been described in the prior art cited in this document. Preference is given to contacting the gas mixture with the absorbent at a pressure of from 1 to 50 bar, preferably from 2 to 20 bar, more preferably from 5 to 10 bar, and a temperature of from 0 to 100° C., in particular from 30 to 50° C. The absorption may be carried out either in columns or in quenching apparatus. It is possible to work in cocurrent or in countercurrent. Examples of useful absorption columns include tray columns (having bubble-cap and/or sieve trays), columns having structured packings (for example sheet metal packings having a specific surface area of from 100 to 1000 $m^2/m^3$, or to 750 $m^2/m^3$, for example Mellapak® 250 Y) and randomly packed columns (for example packed with Raschig packings). It is also possible to use trickle and spray towers, graphite block absorbers, surface absorbers such as thick film and thin film absorbers, and also plate scrubbers, cross-spray scrubbers and rotary scrubbers. It may also be favorable to carry out the absorption in a bubble column with or without internals.

The propane and/or propene can be removed from the absorbent by stripping, flash evaporation (flashing) and/or distillation.

The propane and propene are preferably removed from the absorbent by stripping and/or desorption. The desorption may be carried out in a customary manner by means of a pressure and/or temperature change, preferably at a pressure of from 0.1 to 10 bar, in particular from 1 to 5 bar, more preferably from 1 to 3 bar, and a temperature of from 0 to 200° C., in particular from 20 to 100° C., more preferably from 30 to 70° C., particularly preferably from 40 to 60° C. An example of a gas suitable for stripping is steam, although preference is given in particular to oxygen/nitrogen mixtures, for example air. When air or oxygen/nitrogen mixtures in which the oxygen content is above 10% by volume are used, it may be advisable to add a gas which reduces the explosion range before or during the stripping process. A particularly suitable gas for this purpose is prepurified propane. However, $C_4$ hydrocarbons are to be avoided as such additives according to the invention. Particularly suitable apparatus for the stripping also includes bubble columns with and without internals.

The propane and propene can also be removed from the absorbent by a distillation or rectification, and the columns used may be those familiar to those skilled in the art and have structured packings, random packings or appropriate internals. Preferred conditions in the distillation or rectification are a pressure of from 0.01 to 5 bar, in particular from 0.1 to 4 bar, more preferably from 1 to 3 bar, and a temperature (in the bottom) of from 50 to 300° C., in particular from 150 to 250° C.

Before it is used to charge the at least one partial zone, a gas mixture 1' obtained by stripping from the absorbent may be fed to a further process stage, in order, for example, to reduce the losses of concomitantly stripped absorbent (for example separation in demisters and/or depth filters) and thus at the same time to protect the at least one partial zone from absorbent, or in order to further improve the separating action between the $C_3$ hydrocarbons and the other constituents. Such a removal of the absorbent may be effected by any of the process steps known to those skilled in the art. An example of an embodiment of such a removal which is preferred in the process according to the invention is the quenching of the starting stream from the stripping apparatus with water. In this case, the absorbent is washed out of this laden starting stream with water and the starting stream is at the same time laden with water. This washing or the quenching can be effected, for example, at the top of a desorption column by means of a liquid collecting tray by counterspraying of water, or in a dedicated apparatus.

To promote the separating action, internals increasing the quenching surface area may be installed in the quench chamber, as are known to those skilled in the art from rectifications, absorptions and desorptions.

Water is a preferred washing medium inasfar as it does not normally interfere in the subsequent heterogeneously catalyzed gas phase partial oxidation and/or ammoxidation. After the water has washed the absorbent out of the propane- and propene-laden starting stream, the water/absorbent mixture can be fed to a phase separation and the treated starting stream can be fed in favorable cases as a gas mixture 1'=gas mixture 2 to the heterogeneously catalyzed gas phase partial oxidation and/or ammoxidation.

Both the absorbent stripped to free it of $C_3$ and the absorbent recovered in the phase separation may be reused for the absorption.

In general, the gas mixture 1 and/or the gas mixture 1' obtained therefrom may then be used in a manner known per se in at least one further reaction zone to charge a heterogeneously catalyzed gas phase oxidation and/or ammoxidation of propene to acrolein and/or acrylic acid and/or acrylonitrile with a charge gas mixture 2. If required, the oxidant added to gas mixture 1 and/or gas mixture 1' may be pure molecular oxygen, air, oxygen-enriched air or any other mixture of oxygen and inert gas. When the partial oxidation is the conversion of propylene to propylene oxide, the procedure may be, for example, as described in EP-A 372 972.

When the partial oxidation is a partial ammoxidation to acrylonitrile, the procedure may be, for example, that of DE-A 2351151. In the case of a partial oxidation of propylene to acrolein and/or acrylic acid, the composition of the gas mixture 2 with additional use of gas mixture 1 and/or 1' (it is also possible to use mixtures of the two, i.e. removal is effected from one portion but not from another) will be adjusted, for example, in such a way in the process according to the invention that the following molar ratios are fulfilled:

propane:propene:$N_2$:$O_2$:$H_2O$:others

=0.5 to 20:1:0.1 to 40:0.1 to 10:0 to 20:0 to 1.

According to the invention, the abovementioned molar ratios are advantageously

=2 to 10:1:0.5 to 20:0.5 to 5:0.01 to 10:0 to 1.

According to the invention, it is also favorable when the abovementioned molar ratios are =3 to 6:1:1 to 10:1 to 3:0.1 to 2:0 to 0.5.

Favorable gas mixtures 2 in accordance with the invention are those which comprise from >0 to 30% by volume, often from ≧0.5 to 25% by volume, in many cases from ≧1 to 20% by volume, frequently from ≧3 to 15% by volume, appropriately from ≧5 to 10% by volume, of steam, since such steam contents promote the $C_2$ outlet which forms the basis of the invention. This is true in particular when the catalyst systems recommended below are used for the heterogeneously catalyzed partial gas phase oxidation and/or ammoxidation (especially in the case of a propylene partial oxidation to acrolein and/or acrylic acid).

Especially in combination with the aforementioned facts (but in principle quite generally), the present invention relates to a present configuration of the process according to the invention in which the prepurified propane required for the process according to the invention is fed directly to the first reaction step of the process according to the invention.

The present invention also relates to advantageous embodiments of the process according to the invention in which the prepurified propane required for the process is at most partly (for example only to an extent of 75%, or only to an extent of 50%, or only to an extent of 25%) to the starting reaction gas mixture for the first reaction step and at least partly (generally the remainder, if appropriate the entirety) directly to the heterogeneously catalyzed gas phase partial oxidation and/or ammoxidation (for example to gas mixture 2).

When the heterogeneously catalyzed gas phase partial oxidation and/or ammoxidation comprises a plurality of reaction steps, there may be a direct feed (of a portion or of the entirety of the prepurified propane) of prepurified propane into each of these reaction steps.

Direct feeding of prepurified propane (for example at least 25% by weight, or at least 50% by weight, or at least 75% by weight, or 100% by weight of the total requirement of the process according to the invention for prepurified propane) into at least one reaction step of the heterogeneously catalyzed gas phase partial oxidation and/or ammoxidation is particularly beneficial, since it is automatically accompanied in accordance with the invention by deburdening of the first reaction step of $C_2$ HC. It generally also reduces any risk of explosion.

As already mentioned above, the heterogeneously catalyzed gas phase partial oxidation of propylene to acrylic acid with molecular oxygen proceeds in principle in two reaction steps successive along the reaction coordinate, of which the first leads to acrolein and the second from acrolein to acrylic acid.

In a manner known per se, this reaction sequence opens up the possibility of interrupting the process according to the invention at the stage of acrolein (the stage of predominant acrolein formation) and undertaking the target product removal at this stage, or of continuing the process according to the invention until predominant acrylic acid formation and only then undertaking the target product removal.

When the process according to the invention is carried out up to predominant acrylic acid formation, it is advantageous in accordance with the invention to perform the process in two stages, i.e. in two oxidation stages arranged in series, in which case the fixed catalyst bed to be used and preferably also the other reaction conditions, for example the temperature of the catalyst bed, are appropriately optimized in each of the two oxidation stages in relation to the present invention.

Although the multimetal oxides which comprise the elements Mo, Fe, Bi and are particularly suitable in accordance with the invention as active compositions for the catalysts of the first oxidation stage (propylene→acrolein) are also capable to a certain extent of catalyzing the second oxidation stage (acrolein→acrylic acid), preference is given in accordance with the invention for the second oxidation stage to catalysts whose active composition is at least one multimetal oxide comprising the elements Mo and V. The aforementioned multimetal oxide active compositions and all of those which are described below as favorable in accordance with the invention have the feature that they enable the $C_2$ outlet relevant to the invention in a particularly marked manner.

Thus, the process for heterogeneously catalyzed partial oxidation of propylene over catalyst beds (for example fluidized beds or fixed beds), whose catalysts have, as an active composition, at least one multimetal oxide comprising the elements Mo, Fe and Bi, are suitable in particular as an inventive one-stage process for preparing acrolein (and also acrylic acid if appropriate) or as the first reaction stage for the inventive two-stage preparation of acrylic acid.

The realization of the one-stage heterogeneously catalyzed partial oxidation of propylene to acrolein and also acrylic acid if appropriate, or of the two-stage heterogeneously catalyzed partial oxidation of propylene to acrylic acid, with inventive use of gas mixture 2 may be carried out specifically as described in the documents EP-A 700 714 (first reaction stage; as described there, but also in corresponding countercurrent mode of salt bath and starting reaction gas mixture over the tube bundle reactor), EP-A 700 893 (second reaction stage; as described there, but also in corresponding countercurrent mode), WO 04/085369 (that document in particular is regarded as an integral part of this document) (as a two-stage process), WO 04/85363, DE-A 103 13 212 (first reaction stage), EP-A 11 59 248 (as a two-stage process), EP-A 11 59 246 (second reaction stage), EP-A 11 59 247 (as a two-stage process), DE-A 199 48 248 (as a two-stage process), DE-A 101 01 695 (one-stage or two stage), WO 04/085368 (as a two-stage process), DE 10 2004 021 764 (two-stage), WO 04/085362 (first reaction stage), WO 04/085370 (second reaction stage), WO 04/085365 (second reaction stage), WO 04/085367 (two-stage), EP-A 99 06 36, EP-A 10 07 007 and EP-A 11 06 598.

This applies in particular to all working examples present in these documents. They may be carried out as described in these documents, but with the difference that the starting reaction gas mixture used for the first reaction stage (propylene to acrolein) is an inventive gas mixture 2. Regarding the remaining parameters, the procedure is as described in the working examples of the documents mentioned (in particular regarding the fixed catalyst beds and reactant hourly space velocity on the fixed catalyst beds). When the procedure in the aforementioned working examples of the prior art is two-stage and there is secondary oxygen (secondary air) feeding between the two reaction stages, the feeding is undertaken in an appropriate manner, but its rate is adjusted to the effect that the molar ratio of molecular oxygen to acrolein in the charge gas mixture of the second reaction stage corresponds to that in the working examples of the documents mentioned.

Multimetal oxide catalysts particularly suitable for the particular reaction stage have been described many times and are well known to those skilled in the art. For example, EP-A 253 409 refers on page 5 to appropriate US patents.

Catalysts favorable in accordance with the invention for the particular oxidation stage are also disclosed by DE-A 44 31 957, DE-A 10 2004 025 445 and DE-A 4 431 949. This applies in particular to those of the general formula I in the two aforementioned documents. Catalysts particularly advantageous in accordance with the invention for the particular oxidation stage are disclosed by the documents DE-A 103 25 488, DE-A 103 25 487, DE-A 103 53 954, DE-A 103 44 149, DE-A 103 51 269, DE-A 103 50 812 and DE-A 103 50 822.

For the inventive reaction stage of the heterogeneously catalyzed gas phase partial oxidation of propylene to acrolein or acrylic acid or a mixture thereof, useful multimetal oxide compositions are, as already stated, in principle all multimetal oxide compositions comprising Mo, Bi and Fe.

These are in particular the multimetal oxide active compositions of the general formula I of DE-A 199 55 176, the multimetal oxide active compositions of the general formula I of DE-A 199 48 523, the multimetal oxide active compositions of the general formulae I, II and III of DE-A 101 01 695, the multimetal oxide active compositions of the general formulae I, II and III of DE-A 199 48 248 and the multimetal oxide active compositions of the general formulae I, II and III of DE-A 199 55 168 and also the multimetal oxide active compositions specified in EP-A 700 714.

Also suitable for this reaction step are the multimetal oxide catalysts comprising Mo, Bi and Fe which are disclosed in the documents DE-A 100 46 957, DE-A 100 63 162, DE-C 3 338 380, DE-A 199 02 562, EP-A 015 565, DE-C 2.380 765, EP-A 807 465, EP-A 279 374, DE-A 33 00 044, EP-A 575 897, U.S. Pat. No. 4,438,217, DE-A 198 55 913, WO 98/24746, DE-A 197 46 210 (those of the general formula II), JP-A 91/294239, EP-A 293 224 and EP-A 700 714. This applies in particular to the exemplary embodiments in these documents, among which particular preference is given in accordance with the invention to those of EP-A 015 565, EP-A 575 897, DE-A 197 46 210 and DE-A 198 55 913. Particular emphasis is given in this context to a catalyst according to example 1 c from EP-A 015 565 and also to a catalyst to be prepared in a corresponding manner but whose active composition has the composition $Mo_{12}Ni_{6.5}Zn_2Fe_2Bi_1P_{0.0065}K_{0.06}O_x \cdot 10\ SiO_2$. Emphasis is also given to the example having the serial number 3 from DE-A 198 55 913 (stoichiometry: $Mo_{12}Co_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the unsupported multimetal oxide II catalyst according to example 1 of DE-A 197 46 210. Mention should also be made of the multimetal oxide catalysts of U.S. Pat. No. 4,438,217. The latter is especially true when these hollow cylinders have a geometry of 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Further possible catalyst geometries in this context are extrudates (for example length 7.7 mm and diameter 7 mm; or length 6.4 mm and diameter 5.7 mm).

A multitude of the multimetal oxide active compositions suitable for the step from propylene to acrolein and acrylic acid if appropriate can be encompassed by the general formula IV

$$Mo_{12}Bi_aFe_bX^1_cX^2_dX^3_eX^4_fO_n \qquad (IV)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in IV other than oxygen.

They are obtainable in a manner known per se (see, for example, DE-A 4 023 239) and are customarily shaped in substance to give spheres, rings or cylinders or else used in the form of coated catalysts, i.e. preshaped inert support bodies coated with the active composition. It will be appreciated that they may also be used as catalysts in powder form.

Examples of suitable unsupported catalyst geometries include solid cylinders or hollow cylinders having an external diameter and a length of from 2 to 10 mm. In the case of the hollow cylinder, a wall thickness of from 1 to 3 mm is appropriate. It will be appreciated that the unsupported catalyst can also have spherical geometry, in which case the spherical diameter can be from 2 to 10 mm.

A particularly favorable hollow cylinder geometry is 5 mm×3 mm×2 mm (external diameter×length×internal diameter), especially in the case of unsupported catalysts.

It will be appreciated that the pulverulent active composition or its pulverulent precursor composition which is yet to be calcined and/or partially calcined may also be shaped by applying to preshaped inert catalyst supports. The coating of the support bodies to produce the coated catalysts is generally performed in a suitable rotatable vessel, as disclosed, for example, by DE-A 29 09 671, EP-A 293 859 or EP-A 714 700. To coat the support bodies, the powder composition to be applied is appropriately moistened and dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention is based. The support bodies can have a regular or irregular shape, although preference is given to regularly shaped support bodies having distinct surface roughness, for example spheres or hollow cylinders. Suitable support bodies are substantially nonporous, surface-roughened spherical supports made of steatite whose diameter is from 1 to 10 mm or to 8 mm, preferably from 4 to 5 mm. However, suitable support bodies are also cylinders whose length is from 2 to 10 mm and whose external diameter is from 4 to 10 mm. In the case of rings suitable in accordance with the invention as support bodies, the wall thickness is also typically from 1 to 4 mm. Annular support bodies to be used with preference in accordance with the invention have a length of from 2 to 6 mm, an external diameter of from 4 to 8 mm and a wall thickness of from 1 to 2 mm. Support bodies suitable in accordance with the invention are in particular also rings of geometry 7 mm×3 mm×4 mm (external diameter×length×internal diameter). It will be appreciated that the fineness of the catalytically active oxide compositions to be applied to the surface of the support body is adapted to the desired coating thickness (cf. EP-A 714 700).

Multimetal oxide active compositions to be used for the step from propylene to acrolein (and also acrylic acid if appropriate) are also compositions of the general formula V

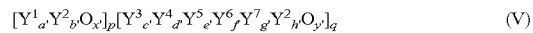

$$[Y^1_{a'}Y^2_{b'}O_{x'}]_p[Y^3_{c'}Y^4_{d'}Y^5_{e'}Y^6_{f'}Y^7_{g'}Y^2_{h'}O_{y'}]_q \qquad (V)$$

in which the variables are each defined as follows:
$Y^1$=only bismuth or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20, e'=from >0 to 20,
f'=from 0 to 6,
g'=from 0 to 15,
h'=from 8 to 16,
x',y'=numbers which are determined by the valency and frequency of the elements in V other than oxygen and
p,q=numbers whose p/q ratio is from 0.1 to 10, comprising three-dimensional regions of the chemical composition $Y^1_a Y^2_{b'} O_{x'}$ which are delimited from their local environment owing to their different composition from their local environment, and whose maximum diameter (longest direct line passing through the center of the region and connecting two points on the surface (interface) of the region) is from 1 nm to 100 μm, frequently from 10 nm to 500 nm or from 1 μm to 50 or 25 μm.

Particularly advantageous inventive multimetal oxide compositions V are those in which $Y^1$ is only bismuth.

Among these, preference is given in turn to those of the general formula VI

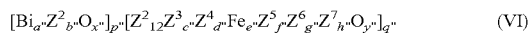 (VI)

in which the variables are each defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a"=from 0.1 to 1,
b"=from 0.2 to 2,
c"=from 3 to 10,
d"=from 0.02 to 2,
e"=from 0.01 to 5, preferably from 0.1 to 3,
f"=from 0 to 5,
g"=from 0 to 10,
h"=from 0 to 1,
x",y"=numbers which are determined by the valency and frequency of the elements in VI other than oxygen,
p",q"=numbers whose p"/q" ratio is from 0.1 to 5, preferably from 0.5 to 2, and very particular preference is given to those compositions VI in which
$Z^2_{b''}$=(tungsten)$_{b''}$ and $Z^2_{12}$=(molybdenum)$_{12}$.

It is also advantageous when at least 25 mol % (preferably at least 50 mol % and more preferably at least 100 mol %) of the total proportion of $[Y^1_a Y^2_{b'} O_{x'}]_p$ ($[Bi_{a''} Z^2_{b''} O_{x''}]_{p''}$) of the multimetal oxide compositions V (multimetal oxide compositions VI) suitable in accordance with the invention is present in the multimetal oxide compositions V (multimetal oxide compositions VI) suitable in accordance with the invention in the form of three-dimensional regions of the chemical composition $Y^1_a Y^2_{b'} O_{x'}$ [$Bi_{a''} Z^2_{b''} O_{x''}$] which are delimited from their local environment owing to their different chemical composition from their local environment, and whose maximum diameter is in the range from 1 nm to 100 μm.

With regard to the shaping, the statements made for the multimetal oxide composition IV catalysts apply to multimetal oxide composition V catalysts.

The preparation of multimetal oxide active compositions V is described, for example, in EP-A 575 897 and also in DE-A 198 55 913.

The inert support materials recommended above are also useful, inter alia, as inert materials for the dilution and/or delimitation of the appropriate fixed catalyst beds, or as a preliminary bed which protects them and/or heats the gas mixture.

It should be mentioned at this point that all catalysts and multimetal oxide compositions which have been recommended as suitable for the step from propylene to acrolein are in principle also suitable for the partial ammoxidation of propylene to acrylonitrile.

For the second step (the second reaction stage), the heterogeneously catalyzed gas phase partial oxidation of acrolein to acrylic acid, useful active compositions are, as already stated, in principle all multimetal oxide compositions comprising Mo and V, for example those of DE-A 100 46 928.

A multitude thereof, for example those of DE-A 198 15 281, can be encompassed by the general formula VII

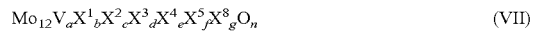 (VII)

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in VII other than oxygen.

Embodiments which are preferred in accordance with the invention among the active multimetal oxides VII are those which are encompassed by the following definitions of the variables of the general formula VII:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in VII other than oxygen.

However, multimetal oxides VII which are very particularly preferred in accordance with the invention are those of the general formula VIII

 (VIII)

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and n'=a number which is determined by the valency and frequency of the elements in VIII other than oxygen.

The multimetal oxide active compositions (VII) which are suitable in accordance with the invention are obtainable in a manner known per se, for example disclosed in DE-A 43 35 973 or in EP-A 714 700.

In principle, multimetal oxide active compositions suitable for the "acrolein→acrylic acid" partial oxidation step, especially those of the general formula VII, can be prepared in a simple manner (like the multimetal oxide active compositions suitable for the first partial oxidation step) by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions VII include those compounds which are already oxides and/or those compounds which can be converted to oxides by heating, at least in the presence of oxygen.

The starting compounds for the preparation of multimetal oxide compositions VII can be intimately mixed in dry or in wet form. When they are mixed in dry form, the starting compounds are appropriately used in the form of finely divided powder and subjected to calcining after mixing and, if appropriate, compaction. However, preference is given to intimate mixing in wet form.

This is typically done by mixing the starting compounds with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, especially those of the general formula VII, may be used for the acrolein oxidation either in powder form or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinders, a wall thickness of from 1 to 3 mm is appropriate. It will be appreciated that the unsupported catalyst may also have spherical geometry, in which case the spherical diameter may be from 2 to 10 mm (e.g. 8.2 mm or 5.1 mm).

It will be appreciated that the pulverulent active composition or its pulverulent precursor composition which is yet to be calcined can also be shaped by applying to preshaped inert catalyst supports. The coating of the support bodies to prepare the coated catalysts is generally performed in a suitable rotatable vessel, as disclosed, for example, by DE-A 2 909 671, EP-A 293 859 or by EP-A 714 700.

To coat the support bodies, the powder composition to be applied is appropriately moistened and is dried again after application, for example by means of hot air. The coating thickness of the powder composition applied to the support body is appropriately selected within the range from 10 to 1000 µm, preferably within the range from 50 to 500 µm and more preferably within the range from 150 to 250 µm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with grit layer. Suitable support bodies include substantially nonporous, surface-roughened, spherical supports made of steatite, whose diameter is from 1 to 10 mm or to 8 mm, preferably from 4 to 5 mm. In other words, suitable spherical geometries may have diameters of 8.2 mm or 5.1 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length×internal diameter). It will be appreciated that the fineness of the catalytically active oxide compositions to be applied to the surface of the support body is adapted to the desired coating thickness (cf. EP-A 714 700).

Favorable multimetal oxide active compositions to be used for the "acrolein→acrylic acid" step are also compositions of the general formula IX $$[D]_p[E]_q \tag{IX}$$

in which the variables are each defined as follows:

$E=Z^7{}_{12}Cu_{h''}H_{i''}O_{y''}$, $Z^1$=W, Nb, Ta, Cr and/or Ce, $Z^2$=Cu, Ni, Co, Fe, Mn and/or Zn, $Z^3$=Sb and/or Bi, $Z^4$=Li, Na, K, Rb, Cs and/or H, $Z^5$=Mg, Ca, Sr and/or Ba, $Z^6$=Si, Al, Ti and/or Zr, $Z^7$=Mo, W, V, Nb and/or Ta, preferably Mo and/or W, a"=from 1 to 8, b"=from 0.2 to 5, c"=from 0 to 23, d"=from 0 to 50, e"=from 0 to 2, f"=from 0 to 5, g"=from 0 to 50, h"=from 4 to 30, i"=from 0 to 20 and x",y"=numbers which are determined by the valency and frequency of the elements in IX other than oxygen and p,q=numbers other than zero whose p/q ratio is from 160:1 to 1:1, and which are obtainable by separately preforming a multimetal oxide composition E

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D $$Mo_{12}V_a \cdot Z^1_{b''} \cdot Z^2_{c''} \cdot Z^3_{d''} \cdot Z^4_{e''} \cdot Z^5_{f''} \cdot Z^6_{g''} \quad (D)$$

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to the multimetal oxide compositions IX in which the preformed solid starting composition 1 is incorporated into an aqueous starting composition 2 at a temperature of <70° C. A detailed description of the preparation of multimetal oxide composition VI catalysts is contained, for example, in EP-A 668 104, DE-A 197 36 105, DE-A 100 46 928, DE-A 197 40 493 and DE-A 195 28 646.

With regard to the shaping, the statements made for the multimetal oxide composition VII catalysts apply to multimetal oxide composition IX catalysts.

Multimetal oxide catalysts which are outstandingly suitable for the "acrolein→acrylic acid" step are also those of DE-A 198 15 281, especially having multimetal oxide active compositions of the general formula I of this document.

Advantageously, unsupported catalyst rings are used for the step from propylene to acrolein and coated catalyst rings for the step from acrolein to acrylic acid.

The process according to the invention, from propylene to acrolein (and also acrylic acid if appropriate), may be carried out with the catalysts described, for example, in a one-zone multiple-catalyst tube fixed bed reactor, as described by DE-A 4 431 957. In this case, gas mixture 2 and heat carrier (heat exchange medium), viewed over the reactor, may be conducted in cocurrent or in countercurrent.

The reaction pressure is typically in the range from 1 to 3 bar and the total hourly space velocity on the fixed catalyst bed with (starting) reaction gas mixture 2 is preferably from 1500 to 4000 or 6000 l (STP/l·h or more. The propylene loading (the propylene hourly space velocity on the fixed catalyst bed) is typically from 90 to 200 l (STP)/l·h or to 300 l (STP)/l·h or more. Propylene loadings above 120, or 130, or 135 l (STP)/l·h or ≧140 l (STP)/l·h, or ≧150 l (STP)/l·h, or ≧160 l (STP)/l·h are particularly preferred in accordance with the invention, since high propylene hourly space velocities cause increased hotspots and thus increased partial oxidation of the $C_2$ HC (all of the aforementioned applies irrespectively of the specific selection of the fixed bed reactor).

The flow to the one-zone multiple catalyst tube fixed bed reactor of the charge gas mixture is preferably from above. The heat exchange medium used is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$).

Viewed over the reactor, as already stated, salt melt and reaction gas mixture 2 may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows (for the flow from bottom to top, the charge sequence is appropriately reversed):

first, to a length of from 40 to 80 or to 60% of the catalyst tube length, either only catalyst or a mixture of catalyst and inert material, the latter, based on the mixture, making up a proportion by weight of up to 20% by weight (section C);

following this, to a length of from 20 to 50 or to 40% of the total tube length, either only catalyst or a mixture of catalyst and inert material, the latter, based on the mixture, making up a proportion by weight of up to 40% by weight (section B); and finally, to a length of from 10 to 20% of the total tube length, a bed of inert material (section A) which is preferably selected such that it causes a very small pressure drop.

Section C is preferably undiluted.

The aforementioned charge variant is especially appropriate when the catalysts used are those according to Example 1 of DE-A 100 46 957 or according to Example 3 of DE-A 100 46 957 and the inert material used is steatite rings having the geometry 7 mm×7 mm×4 mm (external diameter×height× internal diameter). With regard to the salt bath temperature, the statements of DE-A 4 431 957 apply.

However, the inventive partial oxidation, from propylene to acrolein (and acrylic acid if appropriate) may also be carried out with the catalysts described, for example, in a two-zone multiple catalyst tube fixed bed reactor, as described by DE-A 199 10 506 or EP-A 11 06 598. In both of the above-described cases (and also quite generally in the process according to the invention), the propene conversion achieved in single pass is normally at values of ≧90 mol %, or ≧95 mol %, and the selectivity of acrolein formation at values of ≧90 mol %. Advantageously in accordance with the invention, the inventive partial oxidation of propene to acrolein or acrylic acid or a mixture thereof is carried out as described in EP-A 1159244 and most preferably as described in WO 04/085363 and in WO 04/085362, except with the difference that the starting reaction gas mixture used is an inventive gas mixture 2. In particular, all working examples of the aforementioned documents may be carried out as described in these documents, but with use of a gas mixture 2 as the charge gas mixture, especially with the gas mixtures 2 detailed in this document as particularly preferred and as exemplary.

The documents EP-A 1159244, WO 04/085363 and WO 04/085362 are considered to be an integral part of this document.

A preferred embodiment of the inventive partial oxidation of propylene to acrolein, or acrylic acid, or a mixture thereof is a process according to the invention in which gas mixture 2 is conducted over a fixed catalyst bed whose active composition is at least one multimetal oxide comprising the elements Mo, Fe and Bi, with the proviso that the fixed catalyst bed is arranged in two spatially successive temperature zones A, B, both the temperature of temperature zone A and the temperature of temperature zone B are a temperature in the range from 290 to 380° C., the fixed catalyst bed consists of at least two spatially successive fixed catalyst bed zones, the volume-specific activity within one fixed catalyst bed zone being substantially constant and increasing (appropriately sharply) in flow direction of gas mixture 2 at the transition from one fixed catalyst bed zone into another fixed catalyst bed zone, temperature zone A extends up to a conversion of propene of from 40 to 80 mol %, the propene conversion in single pass of gas mixture 2 through the entire fixed catalyst bed is ≧90 mol % and the selectivity of acrolein formation based on converted propene is ≧90 mol %, the time sequence in which gas mixture 2 flows through temperature zones A, B corresponds to the alphabetic sequence of the temperature zones, the hourly space velocity on the fixed catalyst bed of propene present in starting reaction gas mixture 2 is ≧90 l (STP) of propene/l of fixed catalyst bed·h, and the difference $T^{maxA} - T^{maxB}$, formed from the highest temperature $T^{maxA}$ that gas mixture 2 has within temperature zone A and the highest temperature $T^{maxB}$ that gas mixture 2 has within temperature zone B is ≧0° C., and wherein, preferably, in addition, the transition from temperature zone A into temperature zone B in the fixed catalyst bed does not coincide with a transition from one fixed catalyst bed zone into another fixed catalyst bed zone.

Further details of this procedure can be found in WO 04/085362 which is an integral part of this document, and also in the further course of this document in the description of the particularly preferred two-stage partial oxidation of propylene to acrylic acid.

The second step in the case of a two-stage partial oxidation of propylene to acrolein, i.e. the partial oxidation of acrolein to acrylic acid, may be carried out with the catalysts described, for example, in a one-zone multiple catalyst tube fixed bed reactor as described in DE-A 44 31 949. In this reaction stage, reaction gas mixture and heat carrier can be conducted in cocurrent viewed over the reactor. In general, the product gas mixture of the preceding inventive propylene partial oxidation to acrolein may in principle be conducted as such (if appropriate after intermediate cooling (this may be effected indirectly or directly by, for example, secondary air addition) thereof), i.e. without secondary component removal, into the second reaction stage, i.e. into the acrolein partial oxidation.

The molecular oxygen required for the second step, the acrolein partial oxidation, may already be present in gas mixture 2 for the inventive propylene partial oxidation to acrolein. However, it may also be added partly or fully directly to the product gas mixture of the first reaction stage (this is preferably effected in the form of (secondary) air, but may also be effected in the form of pure oxygen or of mixtures of inert gas or oxygen). Irrespective of the procedure, the charge gas mixture of such a partial oxidation of acrolein to acrylic acid advantageously has the following contents:

from 4.5 to 8% by volume of acrolein,
from 2.25 or 4.5% to 9% by volume of molecular oxygen,
from 6 to 30% by volume of propane,
from 32 to 72% by volume of molecular nitrogen,
from 5 to 15% by volume or up to 30% by volume of steam.

The aforementioned charge gas mixture preferably has the following contents:

from 5.5 to 8% by volume of acrolein,
from 2.75 or 5.5 to 9% by volume of molecular oxygen,
from 10 to 25% by volume of propane,
from 40 to 70% by volume of molecular nitrogen,
from 5 to 15% by volume of steam.

The aforementioned charge gas mixture most preferably has the following contents:

from 6 to 8% by volume of acrolein (preferably from 6 to 7% by volume)
from 3 or 6 to 9% by volume of molecular oxygen,
from 10 to 20% by volume of propane (preferably from 10 to 16% by volume),
from 50 to 65% by volume of molecular nitrogen,
from 7 to 13% by volume of steam.

the preferred ranges applying independently of one another, but advantageously being realized simultaneously.

It is further advantageous for aforementioned charge gas mixtures when the molar ratio $V_4$ of molecular oxygen present in the charge gas mixture to acrolein present in the charge gas mixture is ≧0.5 and ≦2, advantageously ≧1 and ≦1.75, particularly advantageously ≧1 and ≦1.5 and most advantageously ≧1 and ≦1.25.

It is further advantageous for aforementioned charge gas mixtures when the molar ratio $V_5$ of propane present in the charge gas mixture to acrolein therein is from 1 to 4, with preference from 1.5 to 3.5, more preferably from 1.5 to 3 and most preferably from 1.5 or 2 to 2.5.

As in the first reaction stage, the reaction pressure in the second reaction stage too is typically in the range from 1 to 3 bar and the total hourly space velocity on the fixed catalyst bed with charge gas mixture is preferably from 1500 to 4000 or 6000 l (STP)/l·h or more. The acrolein loading (the acrolein hourly space velocity on the fixed catalyst bed) is typically from 90 to 190 l (STP)/l·h, or to 290 l (STP)/l·h or more. Acrolein loadings above 110, or 120, or 130, or 135l (STP)/l·h, or ≧140 l (STP)/l·h, or ≧150 l (STP)/l·h, or ≧160 l (STP)/l·h are particularly preferred, since increased hotspots cause an increased inventive $C_2$ HC outlet.

The acrolein conversion based on single pass of the charge gas mixture through the fixed catalyst bed is appropriately normally ≧90 mol % and the accompanying selectivity of acrylic acid formation ≧90 mol %.

The flow to the one-zone multiple catalyst tube fixed bed reactor of the charge gas mixture is likewise preferably from above. The heat exchange medium used in the second stage too is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$). Viewed over the reactor, as already stated, salt melt and charge gas mixture may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows:

first, to a length of from 50 to 80 or to 70% of the catalyst tube length, either only catalyst or a mixture of catalyst and inert material, the latter, based on the mixture, making up a proportion by weight of up to 20% by weight (section C);

thereafter, to a length of from 20 to 40% of the total tube length, either only catalyst or a mixture of catalyst and inert material, the latter, based on the mixture, making up a proportion by weight of up to 50 or up to 40% by weight (section B); and finally, to a length of from 5 to 20% of the total tube length, a bed of inert material (section A) which is preferably selected such that it causes a minimum pressure drop.

Section C is preferably undiluted. As is quite generally the case for the heterogeneously catalyzed gas phase partial oxidation of acrolein to acrylic acid (especially at high acrolein loadings on the fixed catalyst bed and high steam contents of the charge gas mixture), section B may also consist of two successive catalyst dilutions (for the purpose of minimizing hotspot temperature and hotspot temperature sensitivity). From bottom to top, first with up to 20% by weight of inert material and subsequently with from >20% by weight to 50 or to 40% by weight of inert material. Section C is then preferably undiluted.

For flow to the catalyst tubes from bottom to top, the catalyst tube charge is appropriately reversed.

The aforementioned charge variant is especially appropriate when the catalysts used are those according to preparation example 5 of DE-A 100 46 928 or those according to DE-A 198 15 281 and the inert material used is steatite rings having the geometry 7 mm×7 mm×4 mm or 7 mm×7 mm×3 mm (in each case external diameter×height×internal diameter). With regard to the salt bath temperature, the statements of DE-A 443 19 49 apply. It is generally selected in such a way that the acrolein conversion achieved in single pass is normally ≧90 mol %, or ≧95 mol % or ≧99 mol %.

However, the performance of the partial oxidation of acrolein to acrylic acid may also be carried out with the catalysts described, for example, in a two-zone multiple catalyst tube fixed bed reactor as described in DE-199 10 508. For the acrolein conversion, the above statements apply. Also in the case in which an acrolein partial oxidation as described above is carried out as the second stage of a two-stage propylene oxidation to acrylic acid in a two-zone multiple catalyst tube fixed bed reactor, the charge gas mixture for the acrolein partial oxidation will appropriately be obtained directly by using the product gas mixture of the partial oxidation directed to the first step (if appropriate after indirect or direct (for example by supplying secondary air) intermediate cooling thereof) (as has already been described above). The oxygen required for the acrolein partial oxidation is preferably added in the form of air (if appropriate also in the form of pure molecular oxygen or in the form of a mixture of molecular oxygen and an inert gas) and, for example, added directly to the product gas mixture of the first step of the two-stage partial oxidation (propylene→acrolein). However, it may also, as already described, already be present in the gas mixture for the first reaction stage.

In a two-stage partial oxidation of propylene to acrylic acid with direct further use of the product gas mixture of the first step of the partial oxidation to charge the second step of the partial oxidation, two one-zone multiple catalyst tube fixed bed reactors (at high reactant hourly space velocity on the catalyst bed, as is quite generally the case, preference is given to cocurrent mode between reaction gas and salt bath (heat carrier) viewed over the tube bundle reactor) or two two-zone multiple catalyst tube fixed bed reactors will generally be connected in series. A mixed series connection (one-zone/two-zone or vice versa) is also possible.

Between the reactors may be disposed an intermediate cooler which may if appropriate comprise inert beds which can perform a filter function. The salt bath temperature of multiple catalyst tube reactors for the first step of the two-stage partial oxidation of propylene to acrylic acid is generally from 300 to 400° C. The salt bath temperature of multiple catalyst tube reactors for the second step of the partial oxidation of propylene to acrylic acid, the partial oxidation of acrolein to acrylic acid, is usually from 200 to 350° C. In addition, the heat exchange media (preferably salt melts) are normally conducted through the relevant multiple catalyst tube fixed bed reactors in such amounts that the difference between their input and their output temperature is generally ≦5° C. As already mentioned, both steps of the partial oxidation of propylene to acrylic acid may also be implemented in one reactor over one charge, as described in DE-A 101 21 592.

It should also be mentioned once again that a portion of gas mixture 2 for the first step ("propylene→acrolein") may be oxidation cycle gas (residual gas) coming from the partial oxidation.

This is, as already stated, a gas which comprises molecular oxygen and remains after the target product removal (acrolein and/or acrylic acid removal) from the product gas mixture of the partial oxidation and may be recycled partly as inert diluent gas into the charge for the first and/or if appropriate second step of the partial oxidation of propylene to acrolein and/or acrylic acid.

However, such oxidation cycle gas comprising propane, molecular oxygen and, if appropriate, unconverted propylene is advantageously recycled exclusively into the heterogeneously catalyzed propane dehydrogenation which, if appropriate, functions as the propylene source.

Overall, a tube bundle reactor within which the catalyst charge changes appropriately along the individual catalyst tubes with completion of the first reaction step (such two-stage propylene partial oxidations in a single reactor are taught, for example, by EP-A 11 06 598, EP-A 911 313, EP-A 979 813, EP-A 990 636 and DE-A 28 30 765) forms the simplest implementation form of the two oxidation stages for the two steps of the partial oxidation from propylene to acrylic acid. If appropriate, the charge of the catalyst tubes with catalyst is interrupted by an inert material bed.

However, preference is given to implementing the two oxidation stages in the form of two tube bundle systems connected in series. These may be disposed in one reactor, in which case the transition from one tube bundle to the other tube bundle is formed by a bed of inert material which is not accommodated in the catalyst tube (and is appropriately accessible on foot). While the catalyst tubes are generally flowed around by a heat carrier, this does not reach an inert bed accommodated as described above. Advantageously, the two catalyst tube bundles are therefore accommodated in spatially separate reactors. In general, an intermediate cooler is disposed between the two tube bundle reactors in order to reduce any acrolein postcombustion proceeding in the product gas mixture which leaves the first reaction stage. The reaction temperature in the first reaction stage (propylene→acrolein) is generally from 300 to 450° C., preferably from 320 to 390° C. The reaction temperature in the first reaction stage (acrolein→acrylic acid) is generally from 200 to 370° C., frequently from 220 to 330° C. The reaction pressure in both oxidation stages is appropriately from 0.5 to 5 bar, advantageously from 1 to 3 bar. The hourly space velocity (l (STP)/l·h) on the oxidation catalysts of reaction gas in both reaction stages is frequently from 1500 to 2500 l (STP)/l·h or to 4000 l (STP)/l·h. The hourly space velocity of propylene may be from 100 to 200 or 300 and more l (STP)/l·h.

In principle, the two oxidation stages in the process according to the invention may be configured as described, for example, in DE-A 198 37 517, DE-A 199 10 506, DE-A 199 10 508 and DE-A 198 37 519.

In both reaction stages, an excess of molecular oxygen relative to the amount required in accordance with the reaction stoichiometry generally has an advantageous effect on the kinetics of the particular gas phase partial oxidation.

In principle, it is also possible to realize the inventive heterogeneously catalyzed gas phase partial oxidation of propylene to acrylic acid in a single one-zone tube bundle reactor as follows. Both reaction steps proceed in one oxidation reactor which is charged with one or more catalysts whose active composition is a multimetal oxide which comprises the elements Mo, Fe and Bi and is capable of catalyzing the reaction of both reaction steps. This catalyst charge can of course change continuously or abruptly along the reaction coordinate. Of course, it is possible in one embodiment of an inventive two-stage partial oxidation of propylene to acrylic acid in the form of two oxidation stages connected in series to partly or fully remove carbon oxide and steam which have formed as a by-product in the first oxidation stage and are present in the product gas mixture leaving the first oxidation stage from said product gas mixture, if required, before it is passed on into the second oxidation stage. According to the invention, a procedure which does not provide for such a removal will preferably be selected.

Useful sources for an intermediate oxygen feed carried out between the two oxidation stages are, as already stated, in addition to air (preferred), either pure molecular oxygen or molecular oxygen diluted with inert gas such as $CO_2$, CO, noble gases, $N_2$ and/or saturated hydrocarbons.

In the process according to the invention, metering of, for example, cold air to product gas mixture of the first reaction stage (propene→acrolein) can also bring about cooling thereof by a direct route before it is used further as a constituent of a charge gas mixture for the second reaction stage.

Advantageously in accordance with the invention, the partial oxidation of acrolein to acrylic acid is effected as described in EP-A 11 59 246, and most preferably as described in WO 04/085365 and in WO 04/085370. However, preference is given in accordance with the invention to using, as the charge gas mixture comprising acrolein, a charge gas mixture (this may in particular be the product gas mixture of an inventive first-stage partial oxidation of propylene to acrolein), which has if appropriate been supplemented with sufficient secondary air that the ratio of molecular oxygen to acrolein in the resulting charge gas mixture is in each case from 0.5 to 1.5. In particular, all working examples of the aforementioned documents may be carried out as described in these documents, but employing a charge gas mixture according to this document, especially with the charge gas mixtures listed in this document as particularly preferred and as exemplary. The documents EP-A 1159246, WO 04/085365 and WO 04/085370 are regarded as an integral part of this document.

In other words, the inventive partial oxidation of acrolein to acrylic acid can advantageously be carried out with increased acrolein hourly space velocity over a fixed catalyst bed which has at least two temperature zones, as described, for example, in EP-A 11 59 246.

In other words, a particularly preferred embodiment of the inventive partial oxidation of acrolein to acrylic acid is a process according to the invention in which the charge gas mixture comprising acrolein is conducted over a fixed catalyst bed whose active composition is at least one multimetal oxide comprising the elements Mo and V, with the proviso that
  the fixed catalyst bed is arranged in two spatially successive temperature zones C, D,
  both the temperature of temperature zone C and the temperature of temperature zone D are a temperature in the range from 230 to 320° C.,
  the fixed catalyst bed consists of at least two spatially successive fixed catalyst bed zones, the volume-specific activity within one fixed catalyst bed zone being substantially constant and increasing (appropriately sharply) in flow direction of charge gas mixture comprising acrolein at the transition from one fixed catalyst bed zone into another fixed catalyst bed zone,
  temperature zone C extends up to a conversion of acrolein of from 45 to 85 mol %,
  the acrolein conversion in single pass of charge gas mixture comprising acrolein through the entire fixed catalyst bed is $\geq$90 mol % and the selectivity of acrylic acid formation based on converted acrolein is $\geq$90 mol %,
  the time sequence in which charge gas mixture comprising acrolein flows through temperature zones C, D corresponds to the alphabetic sequence of the temperature zones,
  the hourly space velocity on fixed catalyst bed of acrolein present in charge gas mixture is $\geq$70 l (STP) of acrolein/l of fixed catalyst bed·h, and
  the difference $T^{maxC} - T^{maxD}$, formed from the highest temperature $T^{maxC}$ that charge gas mixture comprising acrolein has within temperature zone C and the highest temperature $T^{maxD}$ that charge gas mixture has within temperature zone D, is $\geq$0° C., and wherein, preferably, in addition, the transition from temperature zone C into temperature zone D in the fixed catalyst bed does not coincide with a transition from one fixed catalyst bed zone into another fixed catalyst bed zone.

Further details of this procedure can be found in WO 04/085370 which is an integral part of this document, and also in the further course of this document in the description of the particularly preferred two-stage partial oxidation of propylene to acrylic acid.

Such a preferred two-stage partial oxidation of propylene to acrylic acid may advantageously be carried out as described in EP-A 1159248 and in WO 04/085367, but with the difference that the starting reaction gas mixture used for the first oxidation stage (propylene to acrolein) is an inventive gas mixture 2 (in particular also in the working examples of EP-A 1159248 and of WO 04/085367; both documents form an integral part of this document).

However, it will more preferably be carried out according to WO 04/085369 which is an integral part of this document, but with the difference that the starting reaction gas mixture used for the first oxidation stage (propylene to acrolein) is an inventive gas mixture 2 (in particular also in the working examples of WO 04/085369).

In other words, an inventive gas mixture 2 will first be conducted in a first reaction stage over a fixed catalyst bed 1 whose active composition is at least one multimetal oxide comprising the elements Mo, Fe and Bi, with the proviso that
  fixed catalyst bed 1 is arranged in two spatially successive temperature zones A, B,
  both the temperature of temperature zone A and the temperature of temperature zone B are a temperature in the range from 290 to 380° C.,
  fixed catalyst bed 1 consists of at least two spatially successive fixed catalyst bed zones, the volume-specific activity within one fixed catalyst bed zone being substantially constant and increasing (appropriately sharply) in flow direction of gas mixture 2 at the transition from one fixed catalyst bed zone into another fixed catalyst bed zone,
  temperature zone A extends up to a conversion of propene of from 40 to 80 mol %,
  the propene conversion in single pass of gas mixture 2 through the entire fixed catalyst bed 1 is $\geq$90 mol % and the selectivity of acrolein formation and of acrylic acid by-product formation taken together and based on converted propene is $\geq$90 mol %,
  the time sequence in which gas mixture 2 flows through temperature zones A, B corresponds to the alphabetic sequence of temperature zones A, B, the hourly space velocity on fixed catalyst bed 1 of propene present in starting reaction gas mixture 2 is ≧90 l (STP) of propene/l of fixed catalyst bed 1·h, and the difference $T^{maxA}-T^{maxB}$, formed from the highest temperature $T^{maxA}$ that gas mixture 2 has within temperature zone A and the highest temperature $T^{maxB}$ that gas mixture 2 has within temperature zone B, is ≧0° C., then the temperature of the product gas mixture leaving the first reaction stage will be reduced if appropriate by cooling and if appropriate molecular oxygen and/or inert gas, preferably air if appropriate, will be added to the product gas mixture, and it will subsequently be conducted, as a charge gas mixture which comprises acrolein, molecular oxygen and at least one inert gas and comprises the molecular oxygen and the acrolein in a molar $O_2:C_3H_4O$ ratio of ≧0.5, in a second reaction stage over a fixed catalyst bed 2 whose active composition is at least one multimetal oxide comprising the elements Mo and V, with the proviso that fixed catalyst bed 2 is arranged in two spatially successive temperature zones C, D, both the temperature of temperature zone C and the temperature of temperature zone D are a temperature in the range from 230 to 320° C., fixed catalyst bed 2 consists of at least two spatially successive fixed catalyst bed zones, the volume-specific activity within one fixed catalyst bed zone being substantially constant and increasing (appropriately sharply) in flow direction of charge gas mixture at the transition from one fixed catalyst bed zone into another fixed catalyst bed zone, temperature zone C extends up to a conversion of acrolein of from 45 to 85 mol %, the acrolein conversion in single pass of charge gas mixture through the entire fixed catalyst bed 2 is ≧90 mol % and the selectivity of acrylic acid formation based on propene converted over both reaction stages is ≧80 mol %, the time sequence in which charge gas mixture flows through temperature zones C, D corresponds to the alphabetic sequence of the temperature zones C,D, the hourly space velocity on fixed catalyst bed 2 of acrolein present in charge gas mixture is ≧70 l (STP) of acrolein/l of fixed catalyst bed 2·h, and the difference $T^{maxC}-T^{maxD}$, formed from the highest temperature $T^{maxC}$ that charge gas mixture has within temperature zone C and the highest temperature $T^{maxD}$ that charge gas mixture has within temperature zone D, is ≧0° C., with the preferred proviso that, in the process, neither the transition from temperature zone A into temperature zone B in fixed catalyst bed 1 nor the transition from temperature zone C into temperature zone D in fixed catalyst bed 2 coincides with a transition from one fixed catalyst bed zone into another fixed catalyst bed zone.

In this document, the temperature of a temperature zone refers to the temperature of the portion of the fixed catalyst bed disposed in the temperature zone when the process according to the invention is being performed, but in the absence of a chemical reaction. When this temperature is not constant within the temperature zone, the term temperature of a temperature zone refers to the (numerical) mean of the temperature of the fixed catalyst bed along the reaction zone. It is essential in this context that the individual temperature zones are heated substantially independent of one another.

Since both the heterogeneously catalyzed partial gas phase oxidation of propene to acrolein and the heterogeneously catalyzed partial gas phase oxidation of acrolein to acrylic acid is a markedly exothermic reaction, the temperature of the reaction gas mixtures in reactive pass through fixed catalyst bed 1 and fixed catalyst bed 2 respectively are generally different from the temperature of a temperature zone. They are normally above the temperature of the temperature zone and generally pass through a maximum (hotspot maximum) or decline starting from a maximum value within a temperature zone.

In general, the difference $T^{maxA}-T^{maxB}$ in the process according to the invention will not be more than 80° C. According to the invention, $T^{maxA}-T^{maxB}$ is preferably ≧3° C. and ≦70° C. With very particular preference, $T^{maxA}-T^{maxB}$ in the process according to the invention is ≧20° C. and ≦60° C.

When the process according to the invention is being performed in the case of relatively low (≧90 l (STP)/l·h and ≦160 l (STP)/l·h) propene hourly space velocities on fixed catalyst bed 1, the $T^{maxA}-T^{maxB}$ differences required according to the invention are normally attained when, firstly, both the temperature of reaction zone A and the temperature of reaction zone B are in the range from 290 to 380° C. and, secondly, the difference between the temperature of reaction zone B ($T_B$) and the temperature of reaction zone A ($T_A$), i.e., $T_B-T_A$, is ≦0° C. and ≧-20° C. or ≧-10° C. or ≦0° C. and ≧-5° C., or frequently ≦0° C. and ≧-3° C.

When the process according to the invention is being performed under increased (preferred in accordance with the invention) propene hourly space velocities (≧160 l (STP)/l·h and ≦300 l (STP)/l·h, or ≦600 l (STP)/l·h), the $T^{maxA}-T^{maxB}$ differences required according to the invention are normally attained when, firstly, both the temperature of reaction zone A and the temperature of reaction zone B are in the range from 290 to 380° C. and $T_B-T_A$ is ≧0° C. and ≦50° C., or ≧5° C. and ≦45° C., or ≧10° C. and ≦40° C., or ≧15° C. and ≦30° C. or ≦35° C. (e.g. 20° C. or 25° C.).

The above statement regarding the $T_B-T_A$ temperature differences regularly also applies when the temperature of reaction zone A is within the preferred range of from 305 to 365° C. or within the particularly preferred range of from 310 to 340° C.

The propene hourly space velocity on fixed catalyst bed 1 in the process described may therefore be, for example, ≧90 l (STP)/l·h and ≦300 l (STP)/l·h, or ≧110 l (STP)/l·h and ≦280 l (STP)/l·h or ≧130 l (STP)/l·h and ≦260 l (STP)/l·h, or ≧150 l (STP)/l·h and ≦240 l (STP)/l·h, or ≧170 l (STP)/l·h and ≦920 l (STP)/l·h, or ≧190 l (STP)/l·h and ≦200 l (STP)/l·h.

According to the invention, temperature zone A preferably extends up to a propene conversion of from 50 to 70 mol % or from 60 to 70 mol %.

In general, the difference $T^{maxC}-T^{maxD}$ in the process according to the invention will not be more than 75° C. According to the invention, $T^{maxC}-T^{maxD}$ is preferably ≧3° C. and ≦60° C. Most preferably, $T^{maxC}-T^{maxD}$ in the process according to the invention is ≧5° C. and ≦40° C.

When the process according to the invention is being performed in the case of relatively low (≧70 l (STP)/l·h and ≦150 l (STP)/l·h) acrolein hourly space velocities on fixed catalyst bed 2, the $T^{maxC}-T^{maxD}$ differences required according to the invention are normally attained when, firstly, both the temperature of reaction zone C and the temperature of reaction zone D are in the range from 230 to 320° C. and, secondly, the difference between the temperature of reaction zone D ($T_D$) and the temperature of reaction zone C ($T_C$), i.e., $T_D-T_C$, is ≦0° C. and ≧-20° C. or ≧-10° C. or ≦0° C. and ≧-5° C., or frequently ≦0° C. and ≧-3° C.

When the process according to the invention is being performed under increased propene hourly space velocities and thus simultaneously increased acrolein hourly space velocities ($\geq$150 l (STP)/l·h and $\leq$300 l (STP)/l·h, or $\leq$600 l (STP)/l·h), the $T^{maxC}-T^{maxD}$ differences required according to the invention are normally attained when, firstly, both the temperature of reaction zone C and the temperature of reaction zone D are in the range from 230 to 320° C. and $T_D-T_C$ is $\geq$0° C. and $\leq$40° C., or $\geq$5° C. and $\leq$35° C., or 30° C., or $\geq$10° C. and $\leq$25° C., or $\leq$20° C., or $\leq$15° C.

The above statement regarding the $T_D-T_C$ temperature differences regularly also applies when the temperature of reaction zone C is within the preferred range of from 250 to 300° C. or within the particularly preferred range of from 260 to 280° C.

The acrolein hourly space velocity on fixed catalyst bed 2 in the process according to the invention may therefore be, for example, $\geq$70 l (STP)/l·h or $\geq$90 l (STP)/l·h and $\leq$300 l (STP)/l·h, or $\geq$110 l (STP)/l·h and $\leq$280 l (STP)/l·h or $\geq$130 l (STP)/l·h and $\leq$260 l (STP)/l·h, or $\geq$150 l (STP)/l·h and $\leq$240 l (STP)/l·h, or $\geq$170 l (STP)/l·h and $\leq$220 l (STP)/l·h, or $\geq$190 l (STP)/l·h and $\leq$200 l (STP)/l·h.

According to the invention, temperature zone C preferably extends up to an acrolein conversion of from 50 to 85 mol % or from 60 to 85 mol %.

The working pressure in both reaction stages of the process according to the invention may be either below standard pressure (e.g. down to 0.5 bar) or above standard pressure. Typically, the working pressure in both reaction stages of the process according to the invention will be at values of from 1 to 5 bar, frequently from 1 to 3 bar.

Normally, the reaction pressure will not excess 100 bar in either of the two reaction stages.

In general, the propene conversion of fixed catalyst bed 1 based on single pass in the procedure described will be $\geq$92 mol % or $\geq$94 mol %. The selectivity of product-of-value formation (sum of acrolein formation and acrylic acid by-product formation) in the case of suitable selection (see catalysts recommended in this document) of fixed catalyst bed 1 in a manner known per se will regularly be $\geq$92 mol %, or $\geq$94 mol %, frequently $\geq$95 mol %, or $\geq$96 mol % or $\geq$97 mol %.

In general, the acrolein hourly space velocity on fixed catalyst bed 2 in the above-described process will additionally be about 10 l (STP)/l·h, frequently about 20 or 25 l (STP)/l·h, below the propene hourly space velocity on fixed catalyst bed 1. This can be attributed primarily to the fact that neither the conversion of propene nor the selectivity of acrolein formation generally reach 100%. An additional contribution can arise from secondary oxygen supply.

In general, the acrolein conversion of fixed catalyst bed 2 based on single pass in the above-described process will be $\geq$92 mol %, or $\geq$94 mol %, or $\geq$96 mol %, or $\geq$98 mol % and frequently even $\geq$99 mol % or more.

In the case of suitable selection of fixed catalyst beds 1 and 2 in a manner known per se (see catalyst recommendations given in this document), the selectivity of acrylic acid formation assessed over both reaction stages in the above-described procedure, based on converted propene, will be at values of $\geq$83 mol %, frequently at $\geq$85 mol %, or $\geq$88 mol %, often at $\geq$90 mol %, or $\geq$93 mol %.

It should also be mentioned that an inventive partial oxidation and/or ammoxidation may be carried out in such a way that a reaction gas mixture which does not comprise any oxygen is initially passed over the catalyst charge. In this case, the oxygen required for the partial oxidation is provided in the form of latice oxygen. In a subsequent regeneration step with a gas comprising oxygen (for example air, oxygen-enriched air or oxygen-depleted air), the fixed catalyst bed is regenerated in order subsequently in turn to be available for an oxygen-free reaction gas mixture, etc.

Quite generally, the catalyst beds are selected in the inventive partial oxidation and/or ammoxidation in such a way (for example by dilution with inert material) that the temperature difference between the hot spot maximum of the reaction gas mixture in the individual reaction zones and the particular temperature of the reaction zone generally does not exceed 80° C. Usually, this temperature difference is $\leq$70° C., frequently from 20 to 70° C. Moreover, the catalyst beds are selected for safety reasons in the manner known to those skilled in the art in such a way (for example by dilution with, for example, inert material) that the peak-to-salt temperature sensitivity as defined in EP-A 11 06 598 is $\leq$9° C., or $\leq$7° C., or $\leq$5° C., or $\leq$3° C.

In this document, the hourly space velocity on a catalyst bed catalyzing a reaction step with reaction gas is understood to mean the amount of reaction gas in standard liters (=l (STP); the volume in liters that the corresponding amount of reaction gas would take up under standard conditions (0° C., 1 bar)) which is conducted through one liter of catalyst bed per hour. The hourly space velocity may correspondingly also be based only on one constituent the reaction gas.

The target product P can be removed from the product gas mixture (gas mixture 3) obtained in the heterogeneous catalyzed gas phase partial oxidation and/or partial ammoxidation in at least one removal step in the manner known per se. The procedure is normally to convert the at least one target product P in a basic removal step from the gas phase into the liquid phase (gas mixture 3 is, if appropriate, cooled beforehand). This may be done, for example, by partial or complete, and also, if appropriate, fractional, condensation of the target product P (for example acrolein and/or acrylic acid) and/or by absorption of the at least one target product P from gas mixture 3 into an aqueous or organic solvent (i.e. fractional condensation and/or absorption with water or aqueous solutions may also be employed superimposed on one another). Preference is generally given in accordance with the invention to fractional condensation and/or absorption into water or into aqueous solutions as a basic removal step, since they are generally accompanied by a particularly marked inventive $C_2$ outlet. In the case of acrylic acid and/or acrolein as the target product, suitable absorbents are, for example, water, aqueous solutions of lower carboxylic acids, and also hydrophobic organic solvents such as mixtures of diphenyl and diphenyl ether (e.g. Diphyl®) or mixtures of Diphyl (from 75 to 99.9% by weight) and dimethyl phthalate (from 0.1 to 25% by weight). In the case of acrylic acid, the product gas mixture comprising the target product P (gas mixture 3) will preferably be fractionally condensed. For example, the basic removal (especially in the case of acrylic acid) can be effected as described in the following documents (cf., for example, EP-A 13 88 533, EP-A 13 88 532, DE-A 102 35 847, EP-A 792 867, WO 98/01415, EP-A 10 15 411, EP-A 10 15 410, WO 99/50219, WO 00/53560, WO 02/09839, DE-A 102 35 847, WO 03/041833, DE-A 102 23 058, DE-A 102 43 625, DE-A 103 36 386, EP-A 854 129, U.S. Pat. No. 4,317,926, DE-A 198 37 520, DE-A 196 06 877, DE-A 190 50 1325, DE-A 102 47 240, DE-A 197 40 253, EP-A 695 736, EP-A 982 287, EP-A 10 41 062, EP-A 11 71 46, DE-A 43 08 087, DE-A 43 35 172, DE-A 44 36 243, DE-A 199 24 532, DE-A 103 32 758 and DE-A 199 24 533). An acrylic acid removal may also be undertaken as described in EP-A 982 287, EP-A 982 289, DE-A 103 36 386, DE-A 101 15 277, DE-A 196 06 877, DE-A 19740 252, DE-A 196 27 847, EP-A 920408, EP-A 10 68 174, EP-A 10 66 239, EP-A 10 66 240, WO 00/53560, WO 00/53561, DE-A 100 53 086 and EP-A 982 288. Preference is given to removing as described in FIG. 7 of WO/0196271 or as described in DE-A 10 2004 032 129 and its equivalent patents. Favorable modes of removal are also the processes described in the documents WO 2004/063138, WO 2004/035514, DE-A 102 43 625 and DE-A 102.35 847. Crude acrylic acid obtained in this way can be further processed, for example, as described in the documents WO 01/77056, WO 03/041832, WO 02/055469, WO 03/078378 and WO 03/041833.

The transfer of the at least one target product P into the condensed phase then, substantially in accordance with the invention, generally also transfers subsequent products, formed in the target reaction, of the $C_2$ HC present as secondary components in the reaction gas mixture, for example acetic acid, acetaldehyde and/or acetonitrile; into the condensed phase.

In other words, the target product removal in the process according to the invention is accompanied by a $C_2$ outlet from the cycle method.

For example, it is possible by stripping with air or nitrogen and/or by the route of desorption to remove the $C_2$ components in a comparatively simple manner from the condensed phase comprising the at least one target product P. If appropriate, rectification may be effected subsequently in addition to this removal or exclusively.

A common feature of the above separating processes is that a residual gas stream which comprises substantially those constituents of the product gas mixture (of gas mixture 3) whose boiling point at standard pressure (1 bar) is $\leqq -30°$ C. (i.e. the constituents which are difficult to condense or else volatile) normally remains, for example, at the top of the particular separating column, for example, which comprises separating internals and in whose lower section the product gas mixture comprising the at least one target product is fed, normally after preceding direct and/or indirect cooling thereof.

In the lower section of the separating column, the less volatile constituents of the product gas mixture, including the particular at least one target product P and the secondary components similarly volatile to the target product P, are normally obtained in the condensed phase.

The residual gas constituents are primarily propane, any propylene which has not been converted in the partial oxidation, molecular oxygen and other inert diluent gases which are frequently also used in the partial oxidation, for example nitrogen and carbon dioxide. Depending on the separation process employed, steam may be present in the residual gas only in traces or in amounts of up to 20% by volume or more.

According to the invention, at least a portion (preferably the entire amount, but if appropriate only half, or two thirds, or three quarters, of this entire amount) (preferably having residual gas composition) comprising propane, molecular oxygen and any unconverted propylene, of this main gas residue is recycled as a feed stream comprising propane into the first reaction step (the dehydrogenation) (oxidation cycle gas). However, portions of residual gas may also be recycled into one or into both stages of the partial oxidation and/or be incinerated for the purpose of energy generation.

In the workup of the condensed phase (for the purpose of removing the target product), further residual gases may be obtained, since it will normally be attempted to recycle the total amount of unconverted propane and propylene present in the product gas mixture into the first reaction step and to recover them in the target product removal. Although they generally still comprise propane and, if appropriate, propylene, they frequently no longer comprise any molecular oxygen. Typically, they are recycled, combined with the main residual gas to give an overall residual gas, into the propane dehydrogenation and/or propane oxydehydrogenation which serves as a propylene source. However, it is also possible to separately utilize such further residual gases.

The preferably full recycling of the remaining overall residual gas thus allows continuous conversion of propane to acrylic acid and/or acrolein or to the other target products P in continuous operation.

In this context, it is essential that the recycling described into the dehydrogenation which serves as a propylene source makes it possible to achieve therein a conversion of propane to propylene with virtually one hundred percent selectivity.

The advantageousness of such a procedure exists both at low ($\leqq 30$ mol %) and at high ($\geqq 30$ mol %) dehydrogenation conversions (based on single pass of freshly prepurified propane through the dehydrogenation). Generally, it is favorable in the case of such recycling of oxidation cycle gas when the hydrogen content in the starting reaction gas mixture is in an at least stoichiometric ratio (based on oxygen combustion to water) to the amount of oxygen recycled into this starting reaction gas mixture via the oxidation cycle gas.

Of course, before recycling of oxidation cycle gas or other residual gases into the first reaction step, it is possible to partly or substantially remove constituents other than propane and propylene therefrom (these may, for example, be $O_2$, CO, $CO_2$, $H_2O$, $N_2$, noble gases, lower aldehydes, alkanecarboxylic acids, maleic anhydride, benzaldehyde, etc.). Such a removal may equally be associated with a $C_2$ outlet. However, the application of the inventive preremoval can itself be configured in a simpler and/or smaller way.

For example, such a $C_3$ HC removal, as already described, may be effected by absorption with subsequent desorption and/or stripping (and also absorbent reuse) in a high-boiling hydrophobic organic solvent. Further separation means are adsorption, rectification, membrane processes and partial condensation. Preference would be given to performing such separation processes under elevated pressure.

When dehydrogenation catalysts are used which are sensitive toward oxygen or compounds comprising oxygen, these oxygenates will be removed from the cycle gas before cycle gas is recycled into the first reaction step.

However, such an oxygen removal can also be omitted deliberately in order to raise the reaction mixture to the desired dehydrogenation temperature by partial combustion of the propane in the first reaction step.

The aforementioned cycle gas method can be employed correspondingly when the partial oxidation is a partial ammoxidation of propylene to acrylonitrile or a partial oxidation of propylene to propylene oxide. It can even be employed correspondingly when propane is replaced by isobutane in the dehydrogenation and the resulting isobutene is partially oxidized in a corresponding manner in a partial oxidation to methacrolein and/or methacrylic acid.

It should also be emphasized once again here that acrylic acid is basically removed from a product gas mixture comprising acrylic acid as the target product and (gas mixture 3) obtained in accordance with the invention preferably in such a way that the product gas mixture which has been cooled beforehand if appropriate by direct and/or indirect cooling is fractionally condensed, ascending (for example into itself), in a column comprising separating internals with side draw removal of crude acrylic acid, and/or absorbed by means of water and/or aqueous solution, as described by way of example in WO 2004/035514 and DE-A 10243625. The crude acrylic acid withdrawn is subsequently preferably subjected to a suspension crystallization and the acrylic acid suspension crystals which are formed are preferably removed from remaining mother liquor by means of a wash column. Advantageously, the wash liquid used is the melt of acrylic acid crystals which have been removed beforehand in the wash column. Furthermore, the wash column is preferably one having forced transport of the crystal bed. It is more preferably a hydraulic (for example a TNO wash column) or a mechanical wash column. For specific details, the description of WO 01/77056, WO 03/041832 and WO 03/041833 may be followed. In other words, preference is given to recycling mother liquor which remains into the fractional condensation (cf. also EP-A 10 15 410). The secondary component outlet is normally below the side draw of the crude acrylic acid as a purge stream.

Using only one crystallization stage, it is thus possible to obtain acrylic acid having a purity of $\geq 99.8\%$ by weight which is outstandingly suitable for producing superabsorbents based on poly-Na acrylate. It should also be emphasized that one advantage of the inventive procedure is in principle that, at all points in this document, including the working examples which follow, wherever catalyst charges diluted with inert material are described and/or required, the corresponding catalysts can also be used undiluted for the same bed length.

Otherwise, the profile of requirements laid down in DE-A 102 45 585, and in DE-A 102 46 119 also applies to the process according to the invention.

EXAMPLES

A) Rectificative Preremoval of Crude Propane

The rectification column has an internal diameter of 50 mm and comprises 40 bubble-cap trays (with one bubble-cap each) arranged equidistantly. The distance between two directly adjacent trays is 50 mm. The rectification column including the bubble-cap trays is manufactured from stainless steel. Externally, the rectification column is heat-insulated with a shell made of Armaflex® thickness 25 mm. The column bottom is heated by means of a natural-circulation evaporator (Robert evaporator) to which hot water of temperature 85° C. is supplied as the heat carrier. The crude propane is fed into the rectification column at the seventeenth bubble-cap tray from the bottom.

The crude propane has the following contents:
  95% by weight of propane,
  0.10% by weight of propene,
  1.00% by weight of n-butene,
  3.28% by weight of isobutane,
  0.60% by weight of ethane,
  86 ppm by weight of ethylene and
  96 ppm by weight of 1-butene.
Based on propane present, its $C_2$ HC content is 0.640% by weight.

The number of theoretical plates above the feed point is 10. The number of theoretical plates below the feed point is 8.

The crude propane is fed to the rectification column in an amount of 300 kg/h. It has a pressure of 18 bar and a temperature of 16° C. It is decompressed into the reaction column by means of a throttle device. The bottom temperature is 72° C. at a bottom pressure (upper limit of the liquid phase) of 14.10 bar. The top pressure if 14.01 bar. The top temperature is 41° C. Above the last bubble-cap tray (viewed from below), a cooling coil is installed into the rectification column. Cooling water of temperature 20° C. is fed to it. Via a chimney tray, 0.82 kg/h of prepurified propane are conducted in liquid form out of the rectification column with a temperature of 40° C. at the top of the rectification column.

The prepurified propane has the following contents:
  99.20% by weight of propane,
  0.10% by weight of propene,
  9 ppm by weight of n-butane,
  0.63% by weight of ethane,
  91 ppm by weight of ethylene and
  1 ppm by weight of 1-butene.
Based on propane present, its $C_2$ HC content is 0.644% by weight. 0.53 kg/h of the prepurified propane withdrawn in liquid form is recycled at a temperature of 40° C. as reflux liquid to the uppermost tray of the rectification column.

From the column bottom, 15.9 g/h of bottoms liquid are withdrawn continuously. It has the following contents:
  61.00% by weight of isobutane,
  18.81% by weight of n-butane
  19.98% by weight of propane,
  269 ppm by weight of propene and
  0.18% by weight of 1-butene.
In a second rectification column as described in DE-A 24 13 461, further prepurified propane can be removed from the bottoms liquid. The bottoms liquid of the aforementioned composition is also outstandingly suitable as a cofeed in a cracker for paraffinic hydrocarbons.

B) Two-Stage Partial Oxidation, of Propane to Acrylic Acid in the Presence of $C_2$ HC I. The charge gas mixture for the first fixed bed reactor had the following contents:

|  | % by vol. |
| --- | --- |
| nitrogen | 46.69 |
| oxygen | 11.84 |
| propane | 32.53 |
| propene | 6.81 |
| ethane | 0.07 |
| n-butane | 0.08 |
| isobutane | 0.12 |
| n-butene | 0.05 |
| isobutene | 0.13 |
| hydrogen | 0.07 |
| carbon dioxide | 0.61 |
| water | 1.00 |
| ethylene | 0.00 |
| carbon monoxide | 0.00 |

This was used to charge the first fixed bed reactor at 2128 l (STP)/l·h and at an inlet pressure of 2.1 bar.

1. First fixed bed reactor for the step of partial oxidation of the propene (propylene) to acrolein
Heat exchange medium used: salt melt consisting of
  53% by weight of potassium nitrate,
  40% by weight of sodium nitrite and
  7% by weight of sodium nitrate.
Dimension of the catalyst tube: total length 4200 mm,
  internal diameter 26 mm,
  external diameter 30 mm,
  wall thickness 2 mm.

Reactor: Consisted of a jacketed cylinder made of stainless steel (cylindrical guide tube surrounded by a cylindrical outer vessel). The wall thicknesses were universally from 2 to 5 mm.
  The internal diameter of the outer cylinder was 168 mm. The internal diameter of the guide tube was approx. 60 mm.
  At the top and bottom, the jacketed cylinder was concluded by a lid and bottom respectively.
  The catalyst tube was mounted in the cylindrical vessel and guided through the cylindrical guide to be such that it projected at the top and bottom end thereof (with sealing) through the lid and bottom respectively in each case by 250 mm.
  The heat exchange medium was enclosed in the cylindrical vessel. In order to ensure very uniform thermal boundary conditions at the outer wall of the catalyst tube over the entire catalyst tube length within the cylindrical vessel (3700 mm), the heat exchange medium was circulated by sparging of nitrogen in the cylindrical vessel.
  By means of the ascending nitrogen, the heat exchange medium was conveyed from bottom to top in the cylindrical guide tube in order then to flow back downward in the intermediate space between cylindrical guide tube and cylindrical outer vessel (circulation of equal goodness can also be achieved by pumped circulation (for example propeller pumps)). Electrical heating mounted on the outer jacket controlled the temperature of the heat exchange medium to the desired level. Otherwise, there was air cooling.
Reactor charge: Viewed over the reactor, salt melt and reaction gas mixture were conducted in countercurrent. The reaction gas mixture entered the reactor at the top. It was conducted into each reaction tube at a temperature of 250° C.
  The salt melt entered the cylindrical guide tube at the bottom at a temperature $T^{in}=320°$ C. and left the cylindrical guide tube at a temperature $T^{out}$. The difference between $T^{in}$ and $T^{out}$ was about 2° C. $T^{average}=(T^{in}+T^{out})/2$.
Catalyst tube charge: Section A: length 50 cm
(from top to bottom) Preliminary bed of steatite rings (steatite C 220 from CeramTec) of geometry 7 mm×7 mm×4 mm (external diameter×length×internal diameter).
  Section B: length 100 cm
    Catalyst tube charge with a homogeneous mixture of 30% by weight of steatite rings (steatite C 220 from CeramTec) of geometry 5 mm×3 mm×2 mm (external diameter×length×internal diameter) and 70% by weight of unsupported catalyst from Section C.
  Section C: length 170 cm
    Catalyst charge of annular (5 mm×3 mm×2 mm=external diameter×length×internal diameter) unsupported catalyst according to Example 1 of DE-A 10046957.
  Section D: length 50 cm
    Downstream bed of steatite rings (steatite C 220 from CeramTec) of geometry 7 mm×7 mm×4 mm (external diameter×length×internal diameter).
2. Intermediate cooling and intermediate oxygen feeding
  The product gas mixture leaving the first fixed bed reactor was conducted for the purpose of intermediate cooling (indirectly by means of air) through a connecting tube (length=400 mm, internal diameter=26 mm, wall thickness=2 mm, material=stainless steel) which, mounted centrally for a length of 200 mm, was charged with an inert bed of steatite spheres (Steatite from CeramTec) of diameter from 5 to 6 mm and flanged directly onto the catalyst tube of the first fixed bed reactor.
  The gas mixture entered the connecting tube at a temperature of more than 310° C. and left it at a temperature of about 140° C. Subsequently, 290 l (STP)/h of compressed air as an oxygen source were mixed with the gas mixture.
  The resulting charge gas mixture mixed on a static mixer was fed at a temperature of 220° C. to the fixed bed reactor for the step of partial oxidation of acrolein to acrylic acid.
3. Second fixed bed reactor for the step of partial oxidation of acrolein to acrylic acid
A fixed bed reactor was used which was of identical design to that for the first step. Salt melt and reaction gas mixture were conducted in cocurrent viewed over the reactor. The salt melt entered at the bottom, the reaction gas mixture likewise.
The catalyst tube charge (from bottom to top) was:
  Section A: length 20 cm
    Preliminary bed of steatite rings (steatite C 220 from CeramTec) of geometry 7 mm×7 mm×4 mm (external diameter×length×internal diameter).
  Section B: length 100 cm
    Catalyst charge of a homogeneous mixture of 30% by weight of steatite rings (steatite C 220 from CeramTec) of geometry 7 mm×3 mm×4 mm (external diameter×length×internal diameter) and 70% by weight of coated catalyst from Section C.
  Section C: length 200 cm
    Catalyst charge of annular (7 mm×3 mm×4 mm external diameter×length×internal diameter) coated catalyst according to Preparation Example 5 of DE-A 10046928 (at this point, it is also possible to use analogous coated catalysts and those prepared in a corresponding manner, but whose active composition has a stoichiometry of $Mo_{12}Y_{2.8}W_{1.2}Cu_{2.4}O_x$ or $Mo_{12}V_{3.5}W_{1.3}Cu_{2.4}O_x$).
  Section D: length 50 cm
    Downstream bed of steatite rings (steatite C 220 from CeramTec) of geometry 7 mm×7 mm×4 mm (external diameter×length×internal diameter).
The second reactor was charged with approx. 3850 g/h of charge gas mixture. $T^{average}$ is as defined for the first fixed bed reactor and was 274° C.
The propene conversion in the first reactor was 97.7 mol % and the acrolein conversion in the second reactor was 99.4 mol %.
The contents of the product gas mixture leaving the second fixed bed reactor at a temperature of 283° C. and a pressure of 1.8 bar were:

|  | % by vol. |
| --- | --- |
| nitrogen | 52.87 |
| oxygen | 3.03 |
| propane | 27.48 |
| propene | 0.14 |
| methane | 0 |
| ethane | 0.07 |
| n-butane | 0.08 |
| isobutane | 0.34 |
| n-butene | 0 |
| isobutene | 0 |

-continued

|  | % by vol. |
|---|---|
| 1,3-butadiene | 0 |
| hydrogen | 0.03 |
| carbon monoxide | 0.42 |
| carbon dioxide | 1.85 |
| water | 7.92 |
| acrolein | 0.03 |
| acrylic acid | 5.3 |
| acetic acid | 0.18 |
| formic acid | 0.01 |
| formaldehyde | 0.17 |
| benzaldehyde | 0 |
| maleic anhydride | 0.04 |
| ethane | 0.02 |

II. Example I was repeated with the following differences:
The charge gas mixture of the first reaction stage comprised only 44.6% by volume of nitrogen but 2.1% by volume of ethane.
The product gas mixture leaving the second fixed bed reactor now comprises 0.29% by volume of acetic acid.

III. Example I was repeated with the following differences:
The charge gas mixture of the first reaction stage comprised only 44.7% by volume of nitrogen but 2.0% by volume of ethane.
The product gas mixture leaving the second fixed bed reactor now comprises 0.38% by volume of acetic acid.

U.S. Provisional Patent Application No. 60/679,971, filed on May 12, 2005, is incorporated into the present application by reference.

With reference to the abovementioned teachings, numerous alterations and deviations from the present invention are possible. It may therefore be assumed that the invention, within the scope of the appended claims, may be performed differently than specifically described herein.

What is claimed is:

1. A process for preparing at least one target product P by partial oxidation and/or ammoxidation of propylene, comprising
   a) subjecting prepurified propane, in a first reaction step in the presence of and/or with exclusion of molecular oxygen, to at least one dehydrogenation from the group comprising homogeneous dehydrogenation, heterogeneously catalyzed dehydrogenation, homogeneous oxydehydrogenation and heterogeneously catalyzed oxydehydrogenation to obtain a gas mixture 1 comprising unconverted propane and formed propylene, and
   b) optionally, removing a portion or the entirety of the constituents other than propane and propylene present in the entirety or in a portion of gas mixture 1 therefrom and/or converting them to other compounds to obtain a gas mixture 1' comprising propane and propylene, and, in at least one further reaction step,
   c) subjecting gas mixture 1 or gas mixture 1' or a mixture of formed gas mixture 1' and remaining gas mixture 1, as a constituent of a gas mixture 2, to a heterogeneously catalyzed gas phase partial oxidation and/or partial gas phase ammoxidation of propylene present in gas mixture 1 and/or gas mixture 1' to obtain a gas mixture 3 comprising at least one target product P,
   d) removing target product from gas mixture 3 in at least one removal step and, of the remaining residual gas, recycling at least the propane into the first reaction step, wherein
the prepurified propane is obtained from crude propane which comprises
   $\geq$90% by weight of propane,
   $\leq$99% by weight of propane and propylene,
   $\geq$100 ppm by weight of $C_2$ hydrocarbons and
   $\geq$100 ppm by weight of $C_4$ hydrocarbons,
with the proviso that the crude propane is conducted into a rectification column and the purified propane is removed above the feed point with the proviso that the content of $C_2$ hydrocarbons based on propane present in % by weight in the purified propane is not less than 80% by weight of the corresponding content in the crude propane, and the content of $C_4$ hydrocarbons based on propane present in % by weight in the purified propane is at most 50% by weight of the corresponding content in the crude propane.

2. The process according to claim 1, wherein the crude propane comprises $\geq$200 ppm by weight of $C_2$ hydrocarbons.

3. The process according to claim 1, wherein the crude propane comprises $\geq$500 ppm by weight of $C_2$ hydrocarbons.

4. The process according to claim 1, wherein the crude propane comprises $\geq$800 ppm by weight of $C_2$ hydrocarbons.

5. The process according to claim 1, wherein the crude propane comprises $\geq$1000 ppm by weight of $C_2$ hydrocarbons.

6. The process according to claim 1, wherein the $C_2$ hydrocarbons present in the crude propane comprise at least 90% by weight of ethane and ethylene.

7. The process according to claim 1, wherein the $C_2$ hydrocarbons present in the crude propane comprise at least 94% by weight of ethane and ethylene.

8. The process according to claim 1, wherein the $C_2$ hydrocarbons present in the crude propane comprise at least 50% by weight of ethane.

9. The process according to claim 1, wherein the $C_2$ hydrocarbons present in the crude propane comprise at least 70% by weight of ethane.

10. The process according to claim 1, wherein the $C_2$ hydrocarbons present in the crude propane comprise at least 90% by weight of ethane.

11. The process according to claim 1, wherein the crude propane comprises $\geq$200 by weight of $C_4$ hydrocarbons.

12. The process according to claim 1, wherein the crude propane comprises $\geq$500 by weight of $C_4$ hydrocarbons.

13. The process according to claim 1, wherein the crude propane comprises $\geq$1000 by weight of $C_4$ hydrocarbons.

14. The process according to claim 1, wherein the $C_4$ hydrocarbons present in the crude propane comprise at least 80% by weight of butane.

15. The process according to claim 1, wherein the $C_4$ hydrocarbons present in the crude propane comprise at least 90% by weight of butane.

16. The process according to claim 15, wherein $\geq$50% by weight of the butane present in the crude propane is isobutane.

17. The process according to claim 16, wherein $\geq$70% by weight of the butane present in the crude propane is isobutane.

18. The process according to claim 1, wherein the content of $C_4$ hydrocarbons based on propane present in % by weight in the prepurified propane is at most 30% of the corresponding content in the crude propane.

19. The process according to claim 1, wherein the content of $C_4$ hydrocarbons based on propane present in % by weight in the prepurified propane is at most 10% of the corresponding content in the crude propane.

20. The process according to claim 1, wherein the content of $C_4$ hydrocarbons based on propane present in % by weight in the prepurified propane is at most 1% of the corresponding content in the crude propane.

21. The process according to claim 1, wherein the content based on propane present of $C_2$ hydrocarbons in % by weight in the prepurified propane is not less than 85% by weight of the corresponding content in the crude propane.

22. The process according to claim 1, wherein the content based on propane present of $C_2$ hydrocarbons in % by weight in the prepurified propane is not less than 90% by weight of the corresponding content in the crude propane.

23. The process according to claim 1, wherein the content based on propane present of $C_2$ hydrocarbons in % by weight in the prepurified propane is not less than 95% by weight of the corresponding content in the crude propane.

24. The process according to claim 1, wherein the content based on propane present of $C_2$ hydrocarbons in % by weight in the prepurified propane is not less than 100% by weight of the corresponding content in the crude propane.

25. The process according to claim 1, wherein the content based on propane present of $C_2$ hydrocarbons in % by weight in the prepurified propane is more than 100% by weight of the corresponding content in the crude propane.

26. The process according to claim 1, wherein the content of isobutane in the prepurified propane is $\leq 1000$ ppm by weight.

27. The process according to claim 1, wherein the content of isobutane in the prepurified propane is $\leq 600$ ppm by weight.

28. The process according to claim 1, wherein the content of isobutane in the prepurified propane is $\leq 100$ ppm by weight.

29. The process according to claim 1, wherein the rectification column comprises, as separating internals, mass transfer trays.

30. The process according to claim 1, wherein the rectification column comprises, as separating internals, valve trays.

31. The process according to claim 1, wherein the rectification column has from 5 to 25 theoretical plates.

32. The process according to claim 1, wherein the top pressure in the rectification column is $\geq 5$ bar and $\leq 25$ bar.

33. The process according to claim 1, wherein the bottom temperature in the rectification column is $\leq 100°$ C.

34. The process according to claim 1, wherein the bottom temperature in the rectification column is from 40 to 90° C.

35. The process according to claim 1, wherein the crude propane is fed into the rectification column in such a way that the number of theoretical plates above the feed point is greater than the number of theoretical plates below the feed point.

36. The process according to claim 1, wherein the prepurified propane is withdrawn at the top of the rectification column.

37. The process according to claim 1, wherein the prepurified propane is withdrawn in gaseous form from the rectification column.

38. The process according to claim 1, wherein the rectification column has a water-cooled top condenser.

39. The process according to claim 38, wherein the water is fed to the top condenser with a temperature of $\geq 0°$ C. and $\leq 40°$ C.

40. The process according to claim 1, wherein the prepurified propane is withdrawn in liquid form from the rectification column.

41. The process according to claim 1, wherein the prepurified propane comprises at least 99% by weight of propane, propylene, ethane and ethylene.

42. The process according to claim 1, wherein all reaction steps are carried out in one reaction zone and over a catalyst charge disposed therein.

43. The process according to claim 1, wherein the first reaction step is a heterogeneously catalyzed oxydehydrogenation.

44. The process according to claim 1, wherein the first reaction step is a heterogeneously catalyzed dehydrogenation.

45. The process according to claim 44, wherein the heterogeneously catalyzed dehydrogenation is carried out adiabatically.

46. The process according to claim 44, wherein the heterogeneously catalyzed dehydrogenation is carried out autothermally.

47. The process according to claim 44, wherein the heterogeneously catalyzed dehydrogenation is carried out in a tray reactor.

48. The process according to claim 1, wherein gas mixture 2 comprises from $\geq 0$ to 30% by volume of steam.

49. The process according to claim 1, wherein prepurified propane is fed directly into at least one reaction step of the heterogeneously catalyzed gas phase partial oxidation and/or partial gas phase ammoxidation of propylene.

50. The process according to claim 49, wherein at least 25% by weight of the total requirement for prepurified propane is fed directly to at least one reaction step of the heterogeneously catalyzed gas phase partial oxidation and/or partial gas phase ammoxidation of propylene.

51. The process according to claim 49, wherein at least 50% by weight of the total requirement for prepurified propane is fed directly to at least one reaction step of the heterogeneously catalyzed gas phase partial oxidation and/or partial gas phase ammoxidation of propylene.

52. The process according to claim 1, wherein the target product P is acrolein, acrylonitrile, acrylic acid and/or propylene oxide.

53. The process according to claim 1, wherein gas mixture 2 is subjected to a two-stage heterogeneously catalyzed partial oxidation of the propylene present therein to acrylic acid.

54. The process according to claim 53, wherein propylene is partially oxidized to acrolein in the first partial oxidation stage with the proviso that the partial oxidation is effected over catalysts disposed in a catalyst bed, whose active composition is at least one multimetal oxide of the general formula (IV), $$Mo_{12}Bi_aFe_bX^1{}_cX^2{}_dX^3{}_eX^4{}_fO_n \qquad (IV)$$

where
$X^1$=nickel and/or cobalt,
$X^2$ thallium, an alkali metal and/or an alkaline earth metal,
$X^3$=zinc, phosphorus, boron, antimony, tin, cerium, lead and/or tungsten,
$X^4$=is silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in IV other than oxygen.

55. The process according to claim 53, wherein acrolein is partially oxidized to acrylic acid in the second partial oxidation stage with the proviso that the partial oxidation is effected over catalysts disposed in a catalyst bed whose active composition is at least one multimetal oxide of the general formula (VII)

$$MO_{12}V_aX^1_bV^2_cX^3_dX^4_eX^5_fX^6_gO_n \quad (VII)$$

where
$X^1$=NV, Nb, Ta, Cr and/or Ce,
$X^2$=Cu, Ni, Fe, Mn and/or Zn,
$X^3$=Sb and/or Bi,
$X^4$=one or more alkali metals,
$X^5$=one or more alkali earth metals,
$X^6$=Si, Al, Ti and/or Zr,
a=from 1 to 6,
b=from 0.2 to 4,
c=from 0.5 to 18,
d from 0 to 40,
e=from 0 to 2,
f=from 0 to 4,
g=from 0 to 40 and
n=a number which is determined by the valency and frequency of the elements in VII other than oxygen.

56. The process according to claim 53, wherein the propylene hourly space velocity on the catalyst bed of the first reaction stage is $\geq 120 l(STP)/l \cdot h$.

57. The process according to claim 53, wherein the second reaction stage is charged with a gas mixture which comprises:
from 4.5 to 8% by volume of acrolein,
from 2.25 to 9% by volume of molecular oxygen,
from 6 to 30% by volume of propane,
from 32 to 72% by volume of molecular nitrogen and
from 5 to 30% by volume of steam.

58. The process according to claim 53, wherein the acrolein hourly space velocity on the fixed catalyst bed of the second reaction stage is $\geq 110 l(STP)/l \cdot h$.

59. The process according to claim 53, wherein the reaction temperature in the first reaction stage is from 300 to 450° C.

60. The process according to claim 53, wherein the reaction temperature in the second reaction stage is from 200 to 370° C.

61. The process according to claim 1, wherein the at least one removal step comprises a basic removal step in which the at least one target product P from gas mixture 3 is converted to the liquid phase.

62. The process according to claim 61, wherein the basic removal step comprises a fractional condensation of gas mixture 3 and/or an absorption of the target product P from gas mixture 3 into water or into aqueous solution.

63. The process according to claim 62, wherein the target product P is acrylic acid and the basic removal step is carried out in a column comprising separating internals with side draw removal of crude acrylic acid, and the crude acrylic acid is subjected to a suspension crystallization.

64. The process according to claim 63, wherein the acrylic acid suspension crystals obtained in the suspension crystallization are removed from remaining mother liquor by means of a wash column.

65. The process according to claim 64, wherein the wash column is one with forced transport of the crystal bed.

66. The process according to claim 65, wherein the wash column is a hydraulic wash column.

67. The process according to claim 66, wherein the wash liquid used is the melt of acrylic acid crystals removed beforehand in the wash column.

68. The process according to claim 64, wherein the removed acrylic acid suspension crystals are melted and at least one free-radical polymerization process follows, in which molten acrylic acid crystals are free-radically polymerized to prepare polymers.

69. The process according to claim 1, wherein bottoms liquid is withdrawn continuously from the rectification column and fed as cofeed to a cracker for paraffinic hydrocarbons.

70. The process according to claim 1, wherein bottoms liquid is withdrawn continuously from the rectification column and further treated by rectification.

* * * * *